US006797267B2

(12) United States Patent
Horwitz

(10) Patent No.: US 6,797,267 B2
(45) Date of Patent: Sep. 28, 2004

(54) USE OF CYTOKINES AND MITOGENS TO INHIBIT PATHOLOGICAL IMMUNE RESPONSES

(75) Inventor: David A. Horwitz, Santa Monica, CA (US)

(73) Assignee: University of Southern California, Los Angeles, CA (US)

( * ) Notice: Subject to any disclaimer, the term of this patent is extended or adjusted under 35 U.S.C. 154(b) by 110 days.

(21) Appl. No.: 10/028,944

(22) Filed: Dec. 21, 2001

(65) Prior Publication Data

US 2003/0044765 A1 Mar. 6, 2003

Related U.S. Application Data

(63) Continuation of application No. 09/564,436, filed on May 4, 2000, now Pat. No. 6,358,506, which is a continuation-in-part of application No. 09/186,771, filed on Nov. 5, 1998, now Pat. No. 6,228,359.
(60) Provisional application No. 60/132,616, filed on May 5, 1999, and provisional application No. 60/064,507, filed on Nov. 5, 1997.

(51) Int. Cl.⁷ .............................................. A61K 45/00

(52) U.S. Cl. .................... 424/93.71; 424/85.2; 435/326

(58) Field of Search ........................ 424/93.71, 85.2; 435/326

(56) References Cited

U.S. PATENT DOCUMENTS

| 6,228,359 B1 | 5/2001 | Horwitz |
| 6,358,506 B1 | 3/2002 | Horwitz |
| 6,406,696 B1 | 6/2002 | Bluestone |
| 6,447,765 B1 | 9/2002 | Horwitz |

FOREIGN PATENT DOCUMENTS

| WO | WO 93/17698 | 11/1997 |
| WO | WO 97/42324 | 11/1997 |
| WO | WO 99/25366 A1 | 5/1999 |
| WO | WO 99/48524 | 9/1999 |
| WO | WO 00/66158 A2 | 11/2000 |
| WO | WO 01/16296 | 3/2001 |
| WO | WO 01/77299 | 10/2001 |

OTHER PUBLICATIONS

Anasetti et al., "Treatment of acute graft–versus–host disease with a nonmitogenic anti–CD3 monoclonal antibody", Transplantation 54:844–851 (1992).
Asai O, et al., "Suppression of graft–versus–host disease and amplification of graft–versus–tumor effects by activated natural killer cells after allogeneic bone marrow transplantation," Journal of Clinical Investigation 101(9): 1835–1842 (1998).
Asano M. et al., "Autoimmune disease as a consequence of developmental abnormality of a T cell subpopulation," J Exp Med. Aug. 1, 1996:184(2):387–96.

Auchincloss, Hugh Jr., et al, in Fundamental Immunology 4th Ed., Paul, W.E. (ed.) Lippincot–Raven: Philadelphia, New York;, 1999 pp. 1182–1222.
Barker et al., "Identification of multiple and distinct CD8+ T cell suppressor activities: dichotomy between infected and uninfected individuals, evolution with progression of disease, and sensitivity to gamma irradiation," J Immunol 156:4476–4483 (1996).
Betz, M. and Fox, B.S., "Postaglandin E2 inhibits production of Th1 lymphokines but not of Th2 lymphokines," J Immunol. Jan. 1, 1991:146(1):108–13.
Blazar et al., Both CD4+ and CD8+ T Cells Can Cause Accelerated GVHD Lethality in the Presence of High In Vivo Doses of Exogenous Ill10: Role of Interfereon Gamma (IFNγ) in GVHD Induction, Blood 88:247 (1996) (abstract).
Blazar et al., "FK506 inhibits graft–versus–host disease and bone marrow graft rejection in murine recipients of MHC disparate donor grafts by interfering with mature peripheral T cell expansion post–transplantation," J. Immunol 153: 1836–1846 (1994).
Blazar et al., "Murine recipients of fully mismatched donor marrow are protected form lethal raft–versus–host disease by the in vivo administration of rapamycin but develop an autoimmune–like syndrome", J. Immunol 151:5726–5741 (1993).
Blazar et al., "Recent advances in graft–versus–hosy disease (GVHD)", Immunol Rev 157:79–90 (1997).
Bonig H, et al., "Transforming growth factor–beta 1 suppresses interleukin–15–mediated interferon–gamma production in human T lymphocytes." Scand J Immunol. Dec. 1999:50(6):612–8.
Bonini et al., HSY–TK gene transfer into donor lymphocytes for control of allogeneic graft–versus–leukemia, Science 276:1719–1724 (1997).
Border et al., "Transforming growth factor–beta in disease: the dark side of tissue repair," J Clin Invest 90:1–7 (1992).
Boussiotis et al., "B7 but not intercellular adhesion molecule1 costimulation prevents the induction of human alloantigen–specif tolerance," J Exp Med 178:1753–1763 (1993).
Boussiotis et al., "Allered T–cell receptor + CD28–mediated singnaling and blocked cell cycle progression in interleukin 10 and transforming growth factor–β–treated alloreactive T cells that do not graft–versus–host disease," Blood 97:565–571 (Jan. 2001).

(List continued on next page.)

Primary Examiner—Leon B. Lankford, Jr.
Assistant Examiner—Susan D. Coe
(74) Attorney, Agent, or Firm—Dorsey & Whitney LLP; Renee M. Kosslak; Richard F. Trecartin

(57) ABSTRACT

The invention is generally related to methods of treating autoimmune diseases, including both antibody-mediated and cell-mediated disorders.

26 Claims, 16 Drawing Sheets

OTHER PUBLICATIONS

Bucy, R.P. et al., FASEB J. 1995 9:A497 (Abstract).

Chandrasekar, B., et al., "Dietary calorie restriction inhibits transforming growth factor–beta (TFG–beta) expression in murine lupus nephritis", 9th International Congress on Immunology, 848 (1995).

Chavin et al., "Anti–CD2 mAbs Suppress Cytotoxic Lymphocyte Activity by the Generation of Th2 Suppressor Cells and Receptor Blockade", J Immunol 152:3729–3739 (1994).

Chong P. et al., "Inhibition of protein–kinase C in peripheral blood mononuclear cells of patients with systemic lupus erythematosus: effect on spontaneous immunoglobulin production," Autoimmunity, 10:227–231 (1991).

Cosimi, A.B., et al., "Treatment of acute renal allograft rejection with OKT3 monoclonal antibody," Transplantation Dec. 1981:32(6):525–9.

Delgiudice, G., et al., "TFG–beta activity is increased in systemic lupus erythematosus (SLE) and progressive systemic sclerosis (PSS)", Arthritis and Rheumatism vol. 36 (9 Suppl.) p S 196(Sep. 1993).

Dooms, H. et al., "IL–2 and IL–15 direct the outcome of inappropriate CD4+ T cell stimulation towards apoptosis and anergy respectively," European Cytokine Network, 9(3): 169 (1998).

Dumont et al., "Distinct Mechanisms of Suppression of Murine T Cell Activation by the Related macrolides FK–506 and Rapamycin", J. Immunol 144:251–258 (1990).

Dupont, B., "Immunology of hematopoietic stem cell transplantation: a brief review of its history", Immunol Reviews 157:5–12 (1997).

Fast, "Generation and characterization of IL–2–activated veto cells," J Immunol 149:1510–1515 (1992).

Fernandes, G., et al., "Calorie restriction delays autoimmune murine lupus by differentially modulating oncogenes and TFG–beta–1 expression", 9th International Congress on Immunology., 848 (1995).

Fowler et al., "Donor CD4–enriched cells of Th2 cytokine phenotype regulate graft–versus–host disease without impairing allogeneic engraftment in sublethally irradiated mice", Blood 84:3540–3549 (1994).

Gao Q. et al., "CD4+CD25+ cells regulate CD8 cell anergy in neonatal tolerant mice." Transplantation, Dec. 27, 1999:68(12):1891–7.

Goldman et al., "Bone marrow transplantation for chronic myelogenous leukemia in chronic phase. Increased risk for relapse associated with T–cell depletion", Ann Intern Med 108:806–814 (1988).

Gratama et al., "Treatment of Acute Graft–Versus–Host Disease With Monoclonal Antibody OKT3. Clinical results and effect on circulating T lymphocytes", Transplantation 38(5):469–474 (1984).

Gray et al., "Activated Natural Killer Cells Can Induce Resting B Cells to Produce Immunoglobulin," Arthritis & Rheumatism, 37(9)suppl:S378 (1994).

Gray, J. D., et al., "Generation of an Inhibitory Circuit Involving CD8+ T Cells, IL–2 and NK Cell–Derived TGF–β: Contrasting Effects of Anti–CD2 and Anti–CD3", J. Immunol., 160:2248–2254 (1998).

Gray, J. D., et al., "The Role of Transforming Growth Factor β in the Generation of Suppression: An Interaction between CD8+ T and NK Cells," J. Exp. Med., 180:1937–1942 (Nov. 1994).

Gribben et al., "Complete blockade of B7 family–mediated costimulation is necessary to induce human alloantigen–specific anergy: a method to ameliorate graft–versus–host disease and extend the donor pool", Blood 97:4887–4893 (1996).

Groux, H., et al., "A CD4+ T–cell subset inhibits antigen–specific T–cell responses and prevents colitis," Nature, Oct. 16, 1997:389(6652):737–42.

Hahn, B.H., Dubois'Lupus Erythematosus, 5th Ed. (1997), pp. 69–76 (D.J. Wallace et al. eds., Williams and Wilkins, Baltimore).

Halverson, et al., In Vitro Generation of Allospecific Human CD8+ T Cells of Tc1 and Tc2 Phenotype, Blood 90(5):2089–2096 (1997).

Han, et al., "A New Type of CD4+ Suppressor T cell Completely Prevents Spontaneous Autoimmune Diabetes and Recurrent Diabetes in Syngeneic Islet–Transplanted NOD Mice," Journal of Autoimmunity, 9:331–339 (1996).

Herve et al., "Treatment of Corticosteroid Resistant Acute Graft–Versus–Host Disease by In Vivo Administration of Anti–Interleukin–2 Receptor Monoclonal Antibody (B–B10)", Blood 75(4):1017–1023 (1990).

Hirohata et al., "Role of II–2 in the generation of CD4+ suppressors of human B cell responsiveness", J Immunol 142:3104–3112 (1989).

Hirokawa et al., "Human resting B lymphocytes can serve as accessory cells for anti–CD2–induced T cell activation", J. Immunol. 149:1859–1866, 1992.

Hiruma et al., "Effects of anti–CD3 monoclonal antibody on engraftment of T–cell–depleted bone marrow allografts in mice: host T–cell suppression, growth factors, and space", Blood 79:3050–3058 (1992).

Horwitz DA, et al., "Decreased production of interleukin–12 and other Th1–type cytokines in patients with recent–onset systemic lupus ertthematosus," Arthritis Rheum. May 1998;41(5):838–44.

Horwitz, D. A., et al., "The immunoregulatory effects of NK cells: the role of TGF–β and implications for autoimmunity", Immunology Today, vol. 18(11):538–542 (Nov. 1997).

Horwitz, D.A., Dubois'Lupus Erythematosus, 5th Ed. (1997), pp. 155–194 (D.J. Wallace et al. eds., Williams and Wilkins, Baltimore).

Huggins, M. L., et al., "Modulation of the Autoimmune Response in Lupus Mice by Oral Administration of Attenuated Salmonella typhimurium Expressing the IL–2 and TGF–β Genes", Annals of New York Acad. of Sciences, vol. 815:499–502 (1997).

Jackson AL, et al., "Restricted expression of p55 interleukin 2 receptor (CD25) on normal T cells," Clin Immunol Immunopathol. Jan. 1990;54(1):126–33.

Jonuleit, H., et al., "Induction of interleukin 10–producing, nonproliferating CD4(+) T cells with regulatory properties by repetitive stimulation with allogeneic immature human dendritic cells," J Exp Med. Nov. 6, 2000:192(9):1213–22.

Kanegane H, et al., "A novel subpopulation of CD45RA+ CD4+ T cells expressing IL–2 receptor alpha–chain (CD25) and having a functionally transitional nature into memory cells," Int Immunol. Dec. 3, 1991(12):1349–56.

Kinter et al., "Interleukin 2 induces CD8+ T cell–mediated suppression of human immunodeficiency virus replication in CD4+ T cells and this effect overrides its ability to simulate virus expression", Proc. Natl. Acad. Sci. USA 92:10985–10989 (1995).

Kirk, A.D., et al., "CTLA4–lg and anti–CD40 ligand prevent renal allograft rejection in primates," Proc Natl Acad Sci U S A. Aug. 5, 1997:94(16):8789–94.

Klinman DM, et al., "Quantitation of lgM– and lgG–secreting B cells in the peripheral blood of patients with systemic lupus erythematosus." Arthritis Rheum. Nov. 1991;34(11):1404–10.

Koh et al., "Adoptive cellular immunotherapy: NK cells and bone marrow transplantation," Histol Histopathol 15:1201–1210 (2000).

Koide, J. and Engleman, E.G., "Differences in surface phenotype and mechanism of action between alloantigen–specific CD8+ cytotoxic and suppressor T cell clones," J Immunol. Jan. 1, 1990:144(1):32–40.

Krenger et al., "Effects of exogenous interleukin–10 in a murine model of graft–versus–host disease to minor histocompatibility antigens", Transplantation 58:1251–1257 (1994).

Krenger et al., "Polarized type 2 alloreactive CD4+ and CD8+ donor T cells fail to induce experimental acute graft–versus–host disease", J Immunol 153:585–593 (1995).

Lancaster, F., et al., "Anti–idiotypic T cells suppress rejection of renal allografts in rats," Nature. May 23–29, 1985:315(6017):336–7.

Langrehr, J.M., et al., "Evidence that nitric oxide production by in vivo allosensitized cells inhibits the development of allospecific CTL," Transplantation Mar. 1992;53(3):632–40.

Larsen, C.P., et al., "Long–term acceptance of skin and cardiac allografts after blocking CD40 and CD28 pathways," Nature. May 30, 1996:381(6581):434–8.

Linker–Israeli M, et al., "CD8+ lymphocytes from patients with systemic lupus erythematosus sustain, rather than suppress, spontaneous polyclonal lgG production and synergize with CD4+ cells to support autoantibody synthesis." Arthritis Rheum. Aug. 1990;33(8):1216–25.

Lucas et al., "The development of cellular immunity to Epstein–Barr virus after allogeneic bone marrow transplantation", Blood 87:2594–2603 (1996).

Martin et al., "Effects of in vitro depletion of T cells in HLA–identical allogeneic marrow grafts", Blood 66:664–672 (1985).

Martin et al., "Effects of treating marrow with a CD3–specific immunotoxin for prevention of acute graft–versus–host disease", Bone Marrow Transplant 3:437–444 (1989).

Martin, "Overview of Marrow Transplantation Immunology", in Bone Marrow Transplantation (eds. Forman et al.) pp. 16–21, Boston, Blackwell Scientific Publications (1994).

Martin, P. J. et al., "Treatment of Acute Graft–Versus–Host Disease with Anti–CD3 Monoclonal Antibodies," Am Jour Kidney Disease 11(2):149–152 (1988).

Massague, "Receptors for the TGF–bata family", Cell 69:1067–1070 (1992).

Massague J., "The transforming growth factor–beta family," Annu Rev Cell Biol. 1990;6:597–641.

Mizuochi, T., et al., "Both L3T4+ and Lyt–2+ helper T cells initiate cytotoxic T lymphocyte responses against allogenic major histocompatibility antigens but not against trinitrophenyl–modified self," J Exp Med. 1985 Aug. 1, 1985:162(2):427–43.

Morris, "Prevention and treatment of allograft rejection in vivo by rapamycin: molecular and cellular mechanisms of action", Ann NY Acad Sci 685:68–72 (1993).

Murphy et al., "The potential role of NK cells in the separation of graft–versus–tumor effects from graft–versus–host disease after allogeneic bone marrow transplantation," Immunol Rev 157:167–176 (1997).

Mysliwietz J and Thierfelder S., "Antilymphocytic antibodies and marrow transplantation XII. Suppression of graft–versus–host disease by T–cell–modulating and depleting antimouse CD3 antibody is most effective when preinjected in the marrow recipient," Blood. Nov. 15, 1992;80(10):2661–7 (Abstract).

Ohtsuka, K., eta l., "Decreased Production of TGF–$\beta$ by Lymphocytes from Patients with Systemic Lupus Erythematosus", J. Immunol. 160:2539–2545 (1998).

Oswald, et al., "IL–10 Synergizes with IL–4 and Transforming Growth Factor–Beta to Inhibit macrophage Cytotoxic Activity," J Immunology 148(11):3578–3582 (1992).

Papiernik M. et al., "T cell deletion induced by chronic infection with mouse mammary tumor virus spares a CD25–positive, IL–10–producing T cell population with infectious capacity," J Immunol. May 15, 1997:158(10):4642–53.

Patterson et al., "Graft rejection following HLA matched T–lymphocyte depleted bone marrow transplantation", Br J Haematol 63:221–230 (1986).

Pawelec, et al., "Cytokine Modulation of TH1/TH2 Phenotype Differentiation in Directly Alloresponsive CD4+ Human T Cells," Transplantation, 62(8):1095–1101 (Oct. 1996).

Pearce, N.W., et al., "Specific unresponsiveness in rats with prolonged cardiac allograft survival after treatment with cyclosporine. V. Dependence of CD4+ suppressor cells on the presence of alloantigen and cytokines, including interleukin 2", Transplantation Feb. 1993;:55(2):374–80.

Pescovitz, M.D., et al., "Effect of class II antigen matching on renal allograft survival in miniature swine," J Exp Med. Nov. 1, 1984:60(5):1495–508. Qin L. et al., "Gene transfer for transplantation. Prolongation of allograft survival with transforming growth factor–beta 1," Ann. Surg. Oct. 1994220(4):508–18; discussion 518–9.

Powrie F. et al., "A critical role for transforming growth factor–beta but not interleukin 4 in the suppression of T helper type 1–mediated colitis by CD45RB(low) CD4+ T cells," J Exp Med. 1996 Jun. 1, 1996:183(6):2669–74.

Qin, L., et al., "Gene transfer for transplantation. Prolongation of allograft survival with transforming growth factor–beta 1," Ann Surg. Oct. 1994;220 (4):508–18; discussion 518–9.

Qin, L. et al., "Retrovirus–mediated transfer of viral IL–10 gene prolongs murine cardiac allograft survival," J Immunol. Mar. 15, 1996:156(6):2316–23.

Raju, G.P., et al., "Prolongation of cardiac allograft survival with transforming growth factor–beta 1 in rats," Transplantation. Aug. 15, 1994;58(3):392–6.

Ramsdell, F. and Fowlkes, B.J., "Maintenance of in vivo tolerance by persistence of antigen," Science. Aug. 21, 1992:257(5073);1130–4.

Read S, et al., "Cytotoxic T lymphocyte–associated antigen 4 plays an essential role in the function of CD25(+)CD4(+) regulatory cells that control intestinal inflammation," J Exp Med. Jul. 17, 2000;192(32):295–302.

Rocha, B., et al., "Clonal anergy blocks in vivo growth of mature T cells and can be reversed in the absence of antigen," J Exp Med. May 1, 1993:177(5):1517–21.

Rodt, H., "Anti–lymphocytic antibodies and marrow transplantation 3. Effect of heterologous anti–brain antibodies on acute secondary disease in mice", Eur. J. Immunol 4:25–29 (1974).

Rook et al., "Effects of Transforming Growth Factor β on the Functions of Natural Killer Cells: Depressed Cytolytic Activity and Blunting of Interferon Responsiveness," J Immunology 136(10):3916–3920 (1986).

Roser, B.J., "Cellular mechanisms in neonatal and adult tolerance," Immunol Rev. Feb.1989;107:179–202.

Sakaguchi, S., et al., "Immunologic self–tolerance maintained by activated T cell expressing IL–2 receptor alpha–chains (CD25) Breakdown of a single mechanism of self–tolerance causes various autoimmune diseases," J Immunol. Aug. 1, 1995;155(3):1151–64.

Sakaguchi S, et al., "Organ–specific autoimmune diseases induced in mice by elimination of T cell subset. I. Evidence for the active participation of T cells in natural self–tolerance: deficit of a T cell subset as a possible cause of autoimmune disease," J Exp Med. Jan. 1, 1985;161(1):72–87.

Seddon, B. and Mason, D., "The third function of the thymus," Immunol Today. Feb. 21, 2000;(2):95–9.

Shevach, E.M., "Regulatory T cells in autoimmunity," Annu Rev Immunol 2000;18:423–49.

Shivakumar S. et al., "T cell receptor alpha/beta expressing double–negative (CD4–/CD8–) and CD4+ T helper cells in humans augment the production of pathogenic anti–DNA autoantibodies associated with lupus nephritis," J Immunol. Jul. 1, 1989;143(1):103–12.

Singer, A., et al., "Self recognition in allogeneic radiation bone marrow chimeras. A radiation–resistant host element dictates the self specificity and immune response gene phenotype of T–helper cells," J Exp Med. May 1, 1981;153(5):1286–301.

Snijdewint, F.G., et al., "Prostaglandin E2 differentially modulates cytokine secretion profiles of human T helper lymphocytes," J Immunol. Jun. 15, 1993;150(12):5321–9.

Sporn et al., "Some recent advances in the chemistry and biology of transforming growth factor–beta," J Cell Biol 105:1039–1045 (1987).

Starzl, T.E., et al., "Chimerism and donor–specific nonreactivity 27 to 29 years after kidney allotransplantation," Transplantation, Jun. 1993;55(6):1272–7.

Storb et al., "Long–term follow–up of a controlled trial comparing a combination of methotrexale plus cyclosporine with cyclosporine alone for prophylaxis of graft–versus–host disease in patients administered HLA–identical marrow grafts for leukemia", Blood 80:560–561 (1992).

Strand, V., "Approaches to the management of systemic lupus erythematosus," Current Opinion in Rheumatology, 9:410–420 (1997).

Sullivan et al., "Chronic Graft–Versus–Host Disease and Other Late Complications of Bone Marrow Transplantation", Semin Hematol 28:250–259 (1992).

Suri–Payer E. et al., "CD4+CD25+ T cells inhibit both the induction and effector function of autoreactive T cells and represent a unique lineage of immunoregulatory cells," J Immunol. Feb. 1, 1998;160(3):1212–8.

Suri–Payer E, et al., "Post–thymectomy autoimmune gastritis: fine specificity and pathogenicity of anti–H/K ATPasereactive T Cells," Eur J Immunol. Feb. 1999;29(2):669–77.

Taams, L.S., et al., "Anergic T cells actively suppress T cell responses via the antigen–presenting cell," Eur J Immunol. Sep. 1998;28(9):2902–12.

Takahashi T. et al., "Human CD8+ lymphocytes stimulated in the absence of CD4+ cells enhance IgG production by antibody–secreting B cells," Clin Immunol Immunopathol. Mar. 1991;58(3):352–65.

Takahashi T. et al., "Immunologic self–tolerance maintained by CD25+CD4+ naturally anergic and suppressive T cells: induction of autoimmune disease by breaking their anergic/suppressive state." Int Immunol. Dec. 1998;10(12):1969–80.

Taylor, "Antigen specific suppressor T cells respond to cytokines released by T cells", Advances Exp Med Biol 319:125–135 (1992).

Thornton AM and Shevach EM, "CD4+CD25+ Immunoregulatory T cells suppress polyclonal T cell activation in vitro by inhibiting interleukin 2 production," J Exp Med. Jul. 20, 1998;188(2):287–96.

Thornton AM and Shevach EM. "Suppressor effector function of CD4+CD25+ immunoregulatory T cells is antigen nonspecific." J Immunol. Jan. 1, 2000;164(1):183–90.

Tomita, Y., et al., "Importance of suppressor T cells in cyclophosphamide–induced tolerance to the non–H–2–encoded alloantigens. Is mixed chimerism really required in maintaining a skin allograft tolerance?" J Immunol. Jan. 15, 1990;144(2):463–73.

Vallera et al., "Bone marrow transplantation across major histocompatibility barriers in mice. Effect of elimination of T cells from donor grafts by treatment with monoclonal Thy–1.2 plus complement or antibody alone", Transplantation 31:218–222 (1981).

Vendetti, S. et al., "Anergic T cells inhibit the antigen–presenting function of dendritic cells," J Immunol. Aug. 1, 2000;165(3):1175–81.

Verbanac, K.M. et al., "A role for transforming growth factor–beta in the veto mechanism in transplant tolerance," Transplantation. Mar. 27, 1994;57(6):893–900.

Via et al., "Critical Role of Interleukin–2 in the development of acute graft–versus–host disease", International Immunol 5:565–572 (1993).

Wahl SM. "Transforming growth factor beta: the good, the bad, and the ugly." J Exp Med. Nov. 1, 1994;180(5):1587–90.

Weiner HL., et al., "Oral tolerance: immunologic mechanisms and treatment of animal and human organ–specific autoimmune diseases by oral administration of autoantigens." Annu Rev Immunol. 1994;12:809–37.

Wekerle, T., et al., "Anti–CD154 or CTLA41g obviates the need for thymic irradiation in a non–myeloablative conditioning regimen for the induction of mixed hematopoietic chimerism and tolerance," Transplantation. Nov. 15, 1999;68(9):1348–55.

Wilson, D.B., "Idiotypic regulation of T cells in graft–versus–host disease and autoimmunity," Immunol Rev. Feb. 1989 107:159–77.

Zehavi–Willner et al., "The Mitogenic Activity of Staphylococcal Enterotoxin B (SEB): A Monovalent T Cell Mitogen That Stimulates Cytolytic T Lymphocytes but Cannot Mediate Their Lytic Interaction," Journal of Immunology 137(8):2682–2687 (Oct. 1986).

Zeller, et al., "Induction of CD4+ T Cell Alloantigen–Specific Hyporesponsiveness by IL–10 and TFGβ1," Journal of Immunology 163:3684–3691 (1999).

Zeller, et al., "Ex vivo IL10 and TGF–Beta Act Synergistically to Induce CD4+ Alloantigen–Specific Tolerance Resulting in Diminished Graft–Versus–Host Disease in Vivo," FASEB Journal (Mar. 12, 1999) 12(4)part 1, A614. Meeting info: Annual Meeting of the Professional Research Scientists for Experimental Biology. Apr. 17–21 1999.

Zheng, X.X., et al., "Administration of noncytolytic IL–10/Fc in murine models of lipopolysaccharide–induced septic shock and allogeneic islet transplantation," J Immunol. May 15, 1995;154(10):5590–600.

Chen W., et al., "T cells specific for a polymorphic segment of CD45 induce graft–versus–host disease with predominant pulmonary vasculitis." J Immunol. Jul. 15, 1998;161(2): 909–18.

Early E, and Reen DJ. "Rapid conversion of naive to effector T cell function counteracts diminished primary human newborn T cell responses," Clin Exp Immunol. Jun. 1999;116(3):527–33. (Abstract).

Garderet L, et al., "Effective depletion of alloreactive lymphocytes from peripheral blood mononuclear cell preparations." Transplantation Jan. 15, 1999;67(1):124–30.

Heitger A. et al. "Essential role of the thymus to reconstitue naive (CD45RA+) T–helper cells after human allogeneic bone marrow transplantation." Blood. Jul. 15, 1997;90(2):850–7.

Sykes, M. et al., "In Vitro And In Vivo Analysis Of Bone Marrow–Derived CD3+, CD4–, CD8–, NK1.1+ Cell Lines," Cell Immunol. 129(2):478–93 (1990).

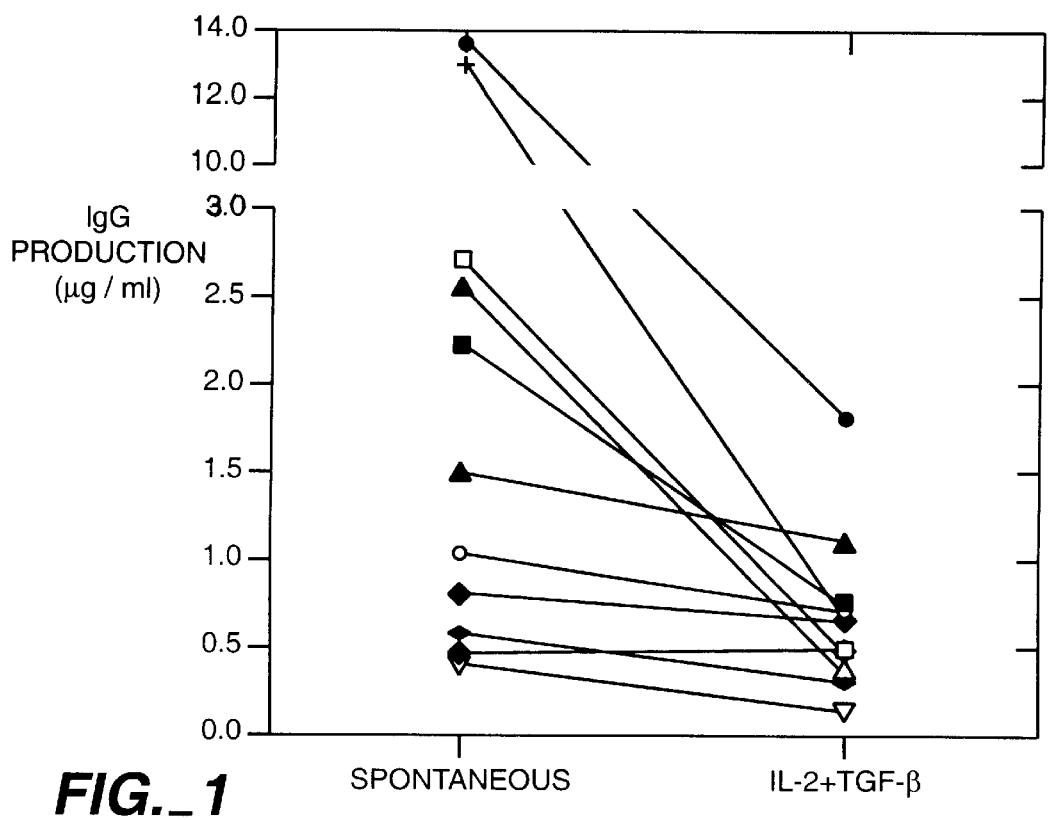
FIG._1
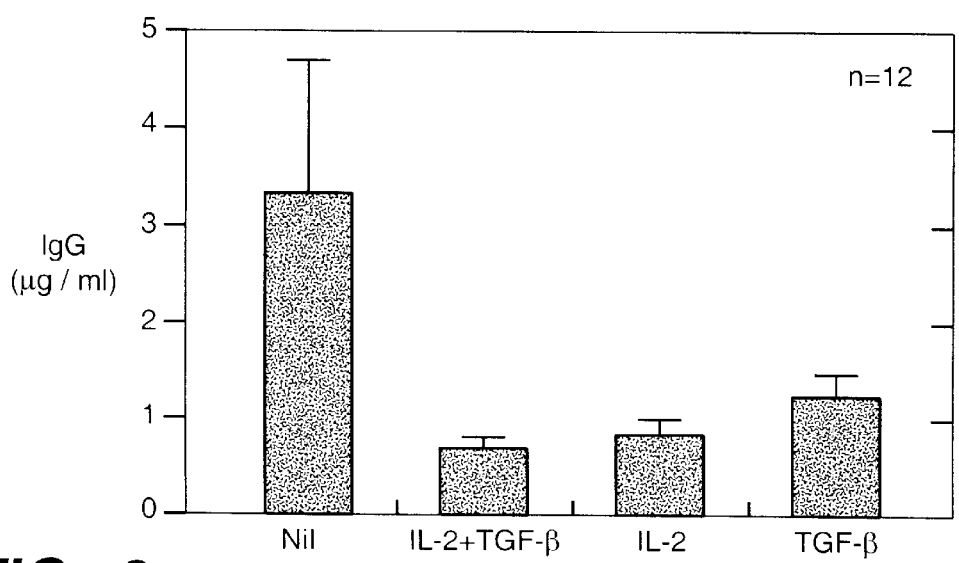
FIG._2

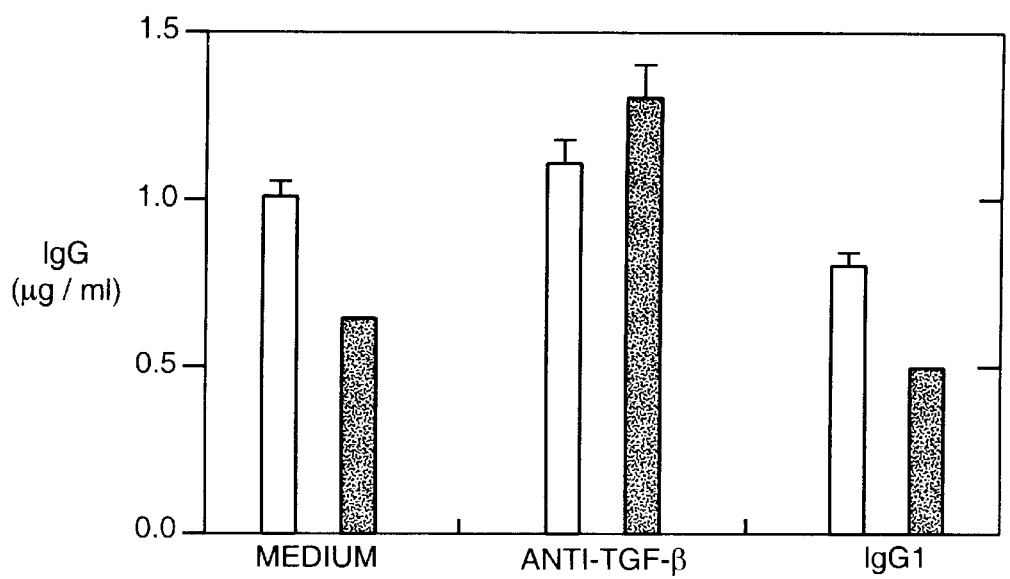
FIG._3A
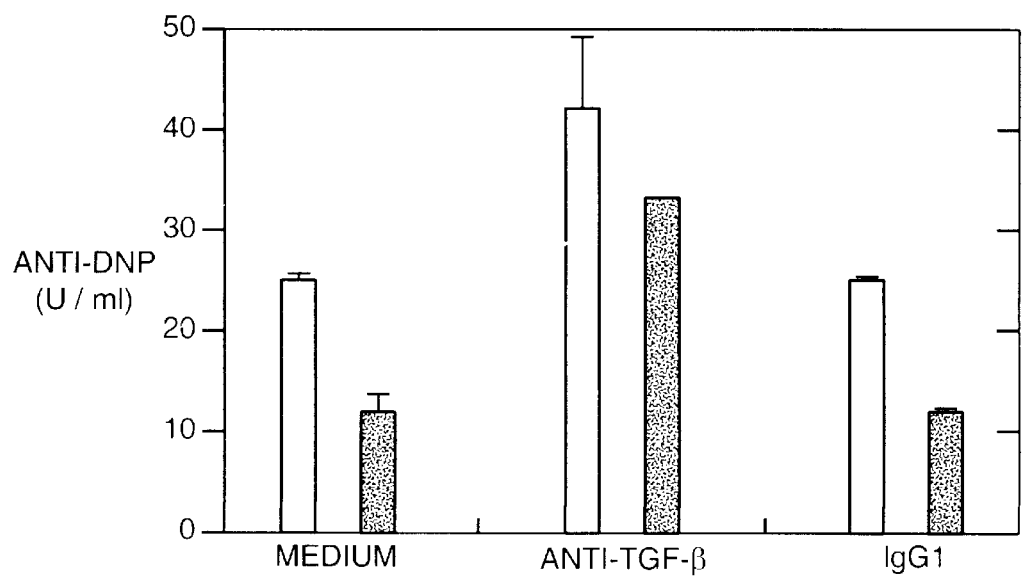
FIG._3B

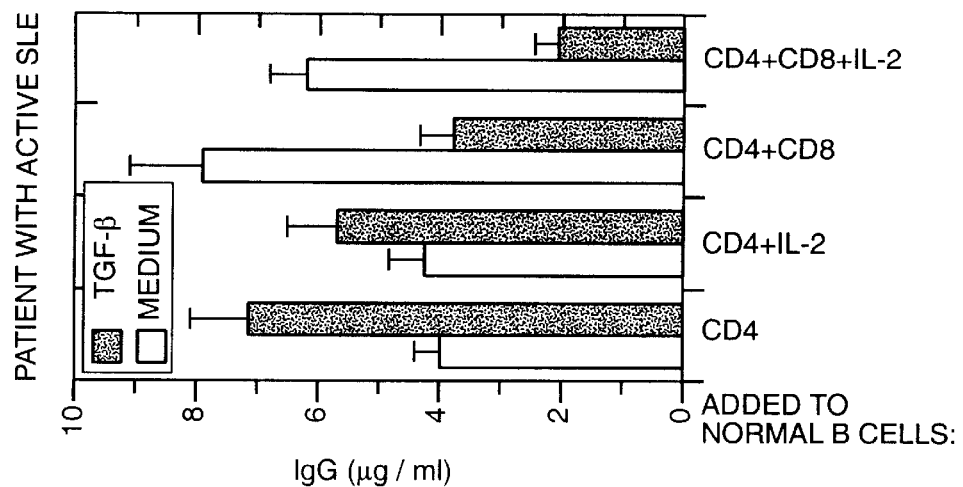
FIG._4C
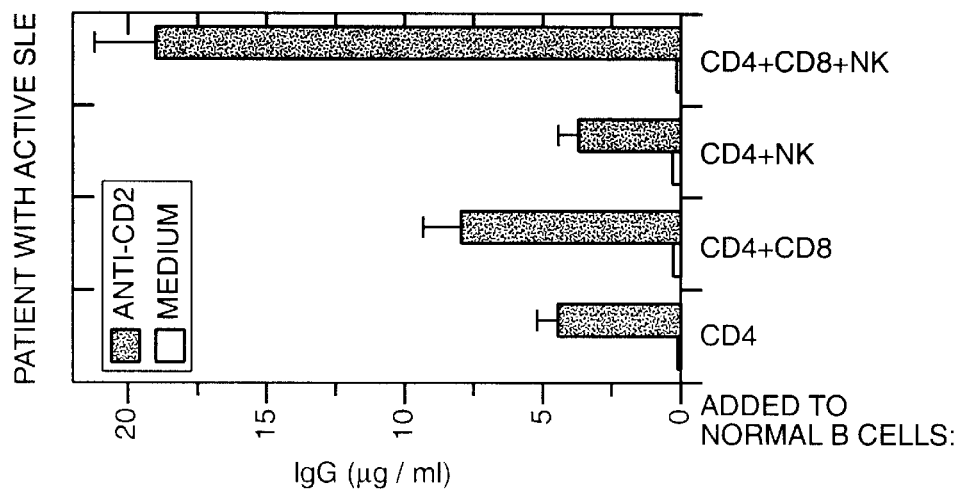
FIG._4B
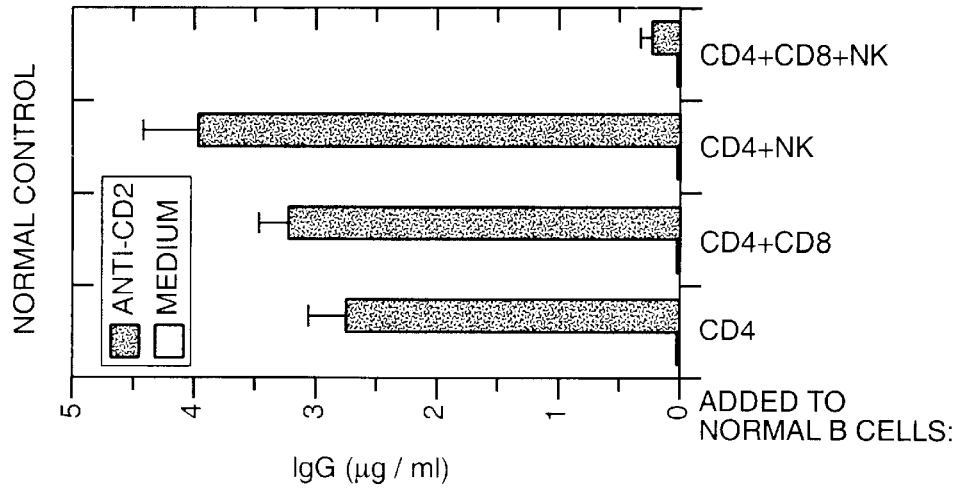
FIG._4A

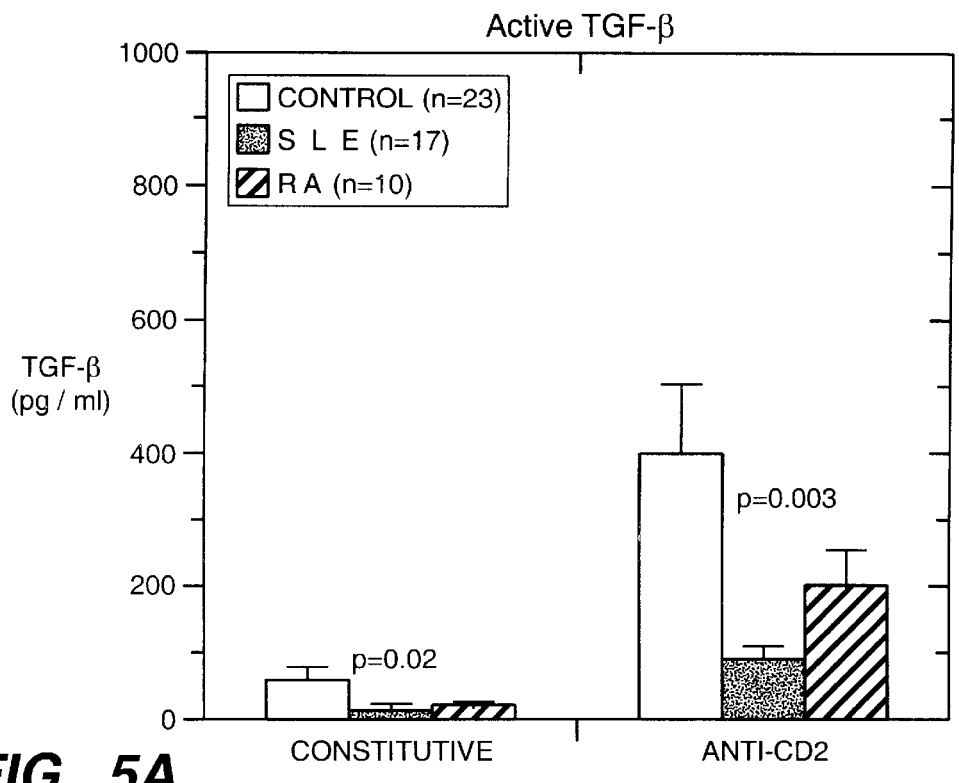
FIG._5A
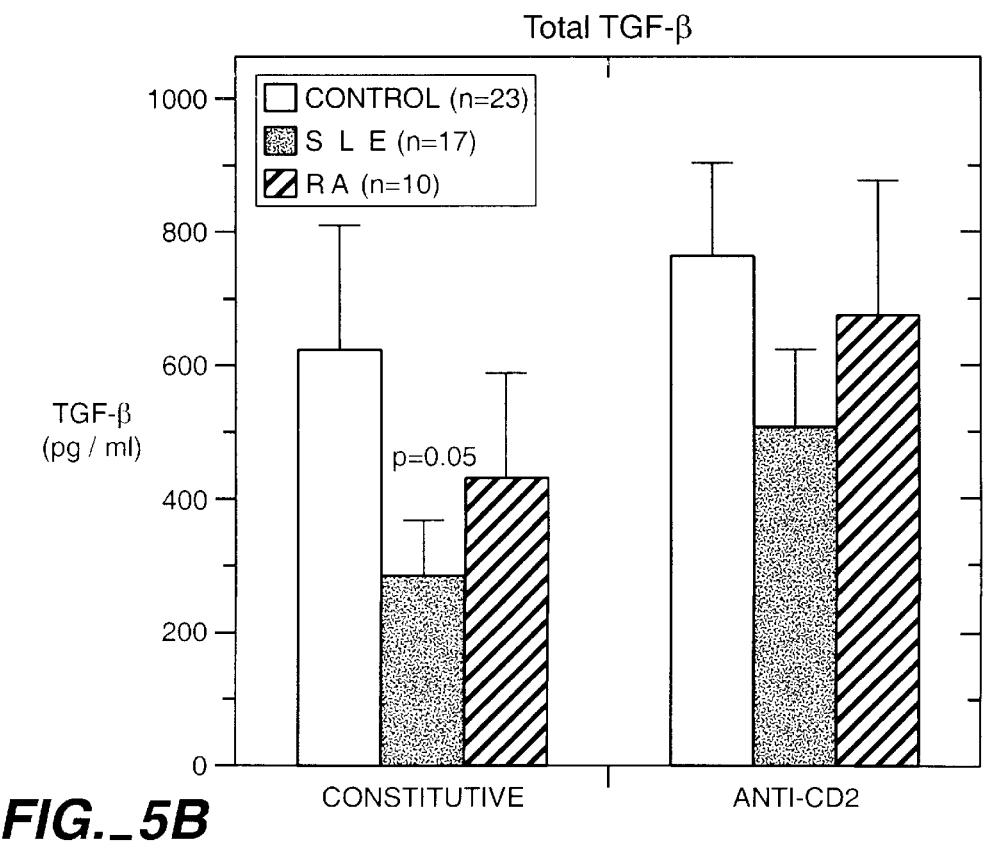
FIG._5B

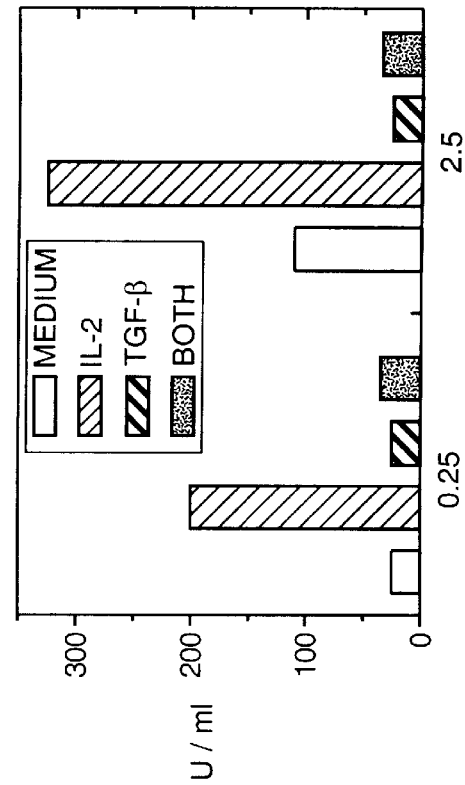
FIG._6B
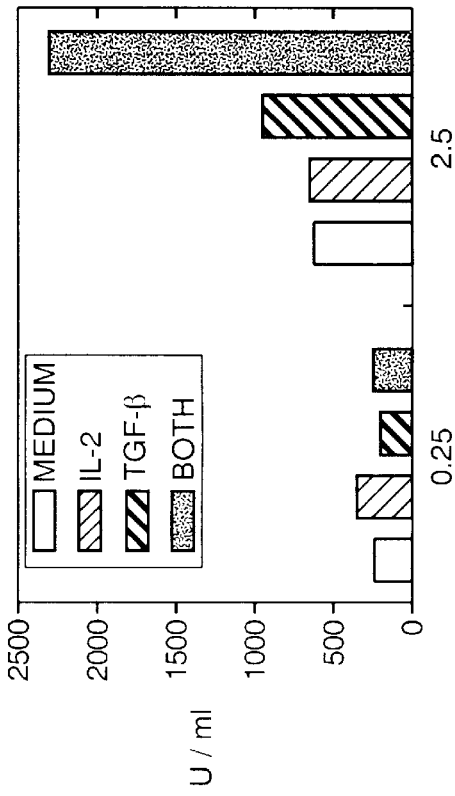
FIG._6A

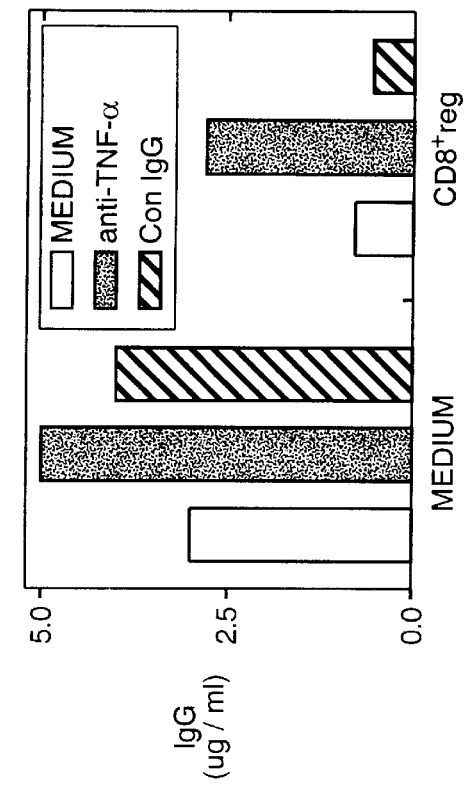
FIG._7B
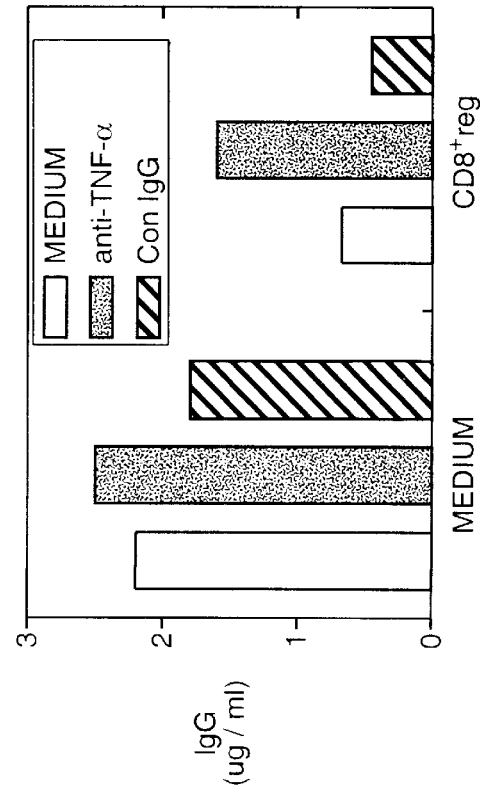
FIG._7A

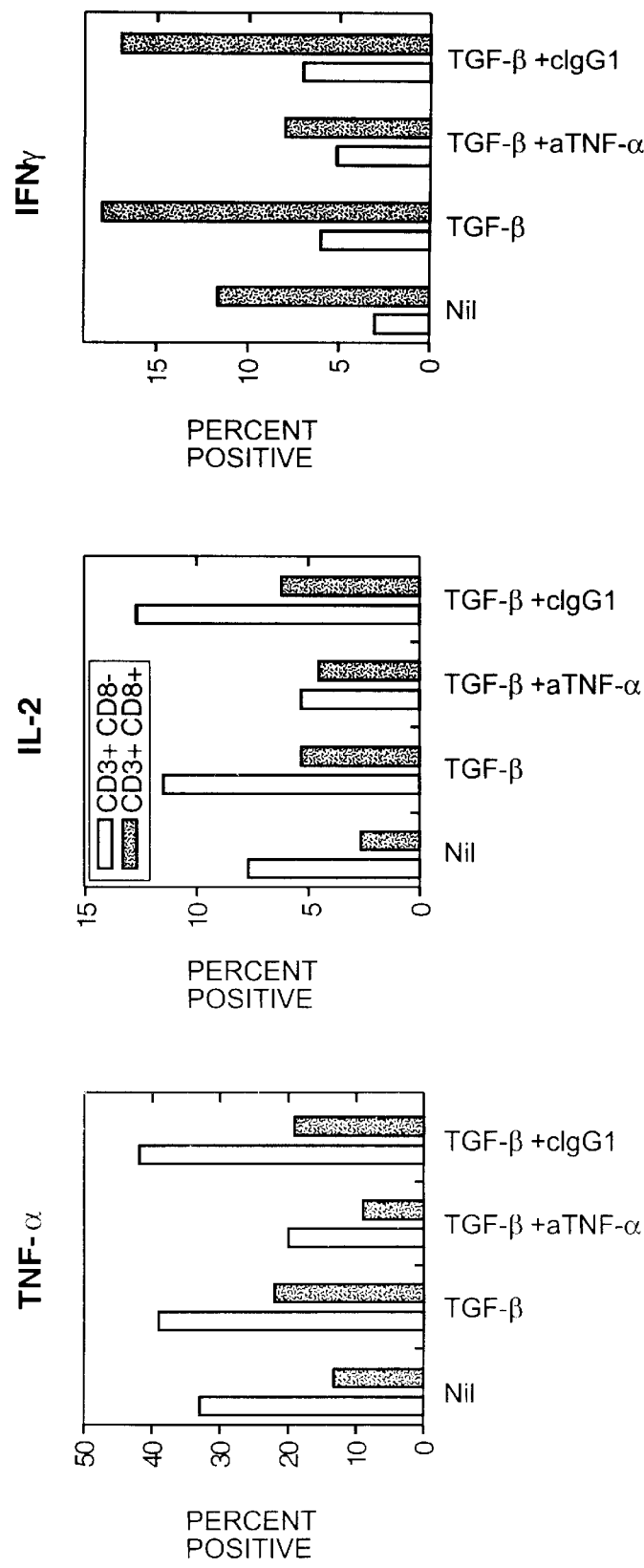

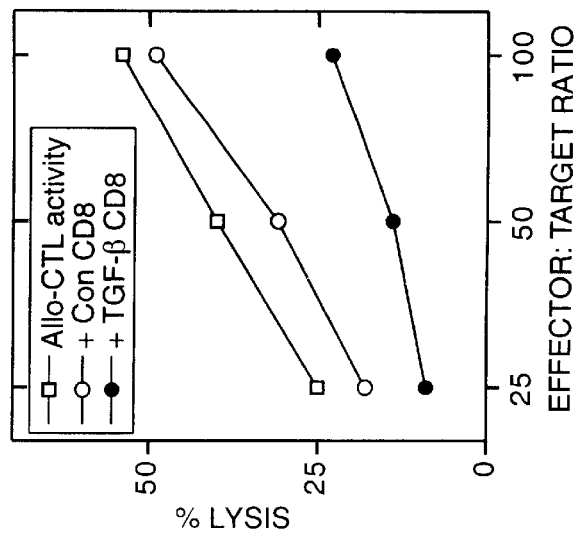
FIG._9C
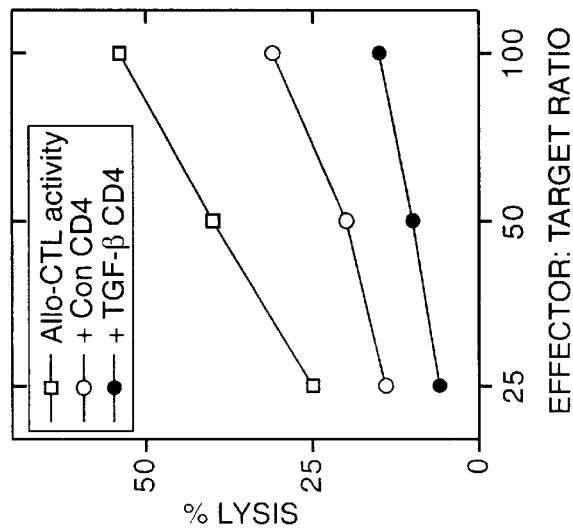
FIG._9B
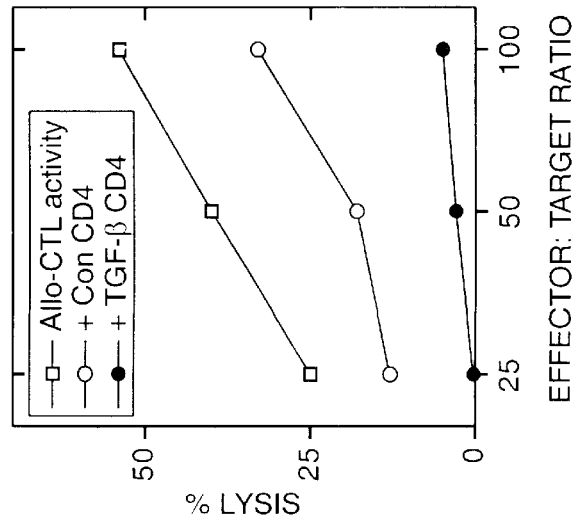
FIG._9A

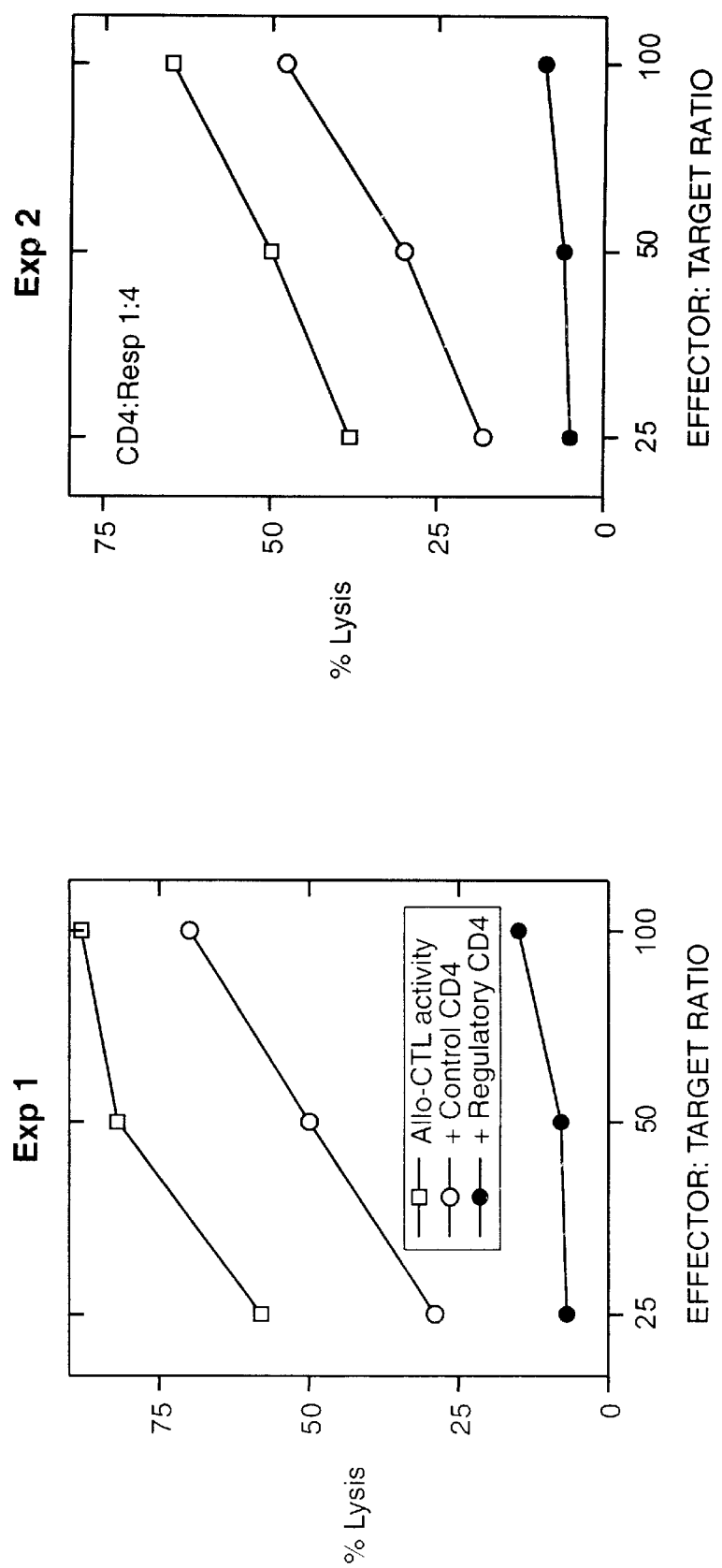

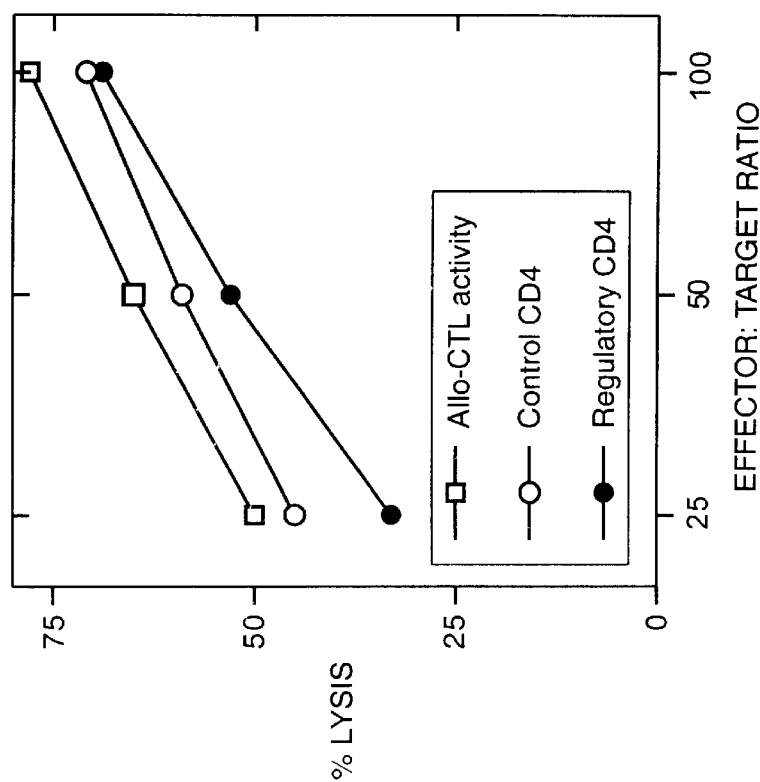
FIG._11B
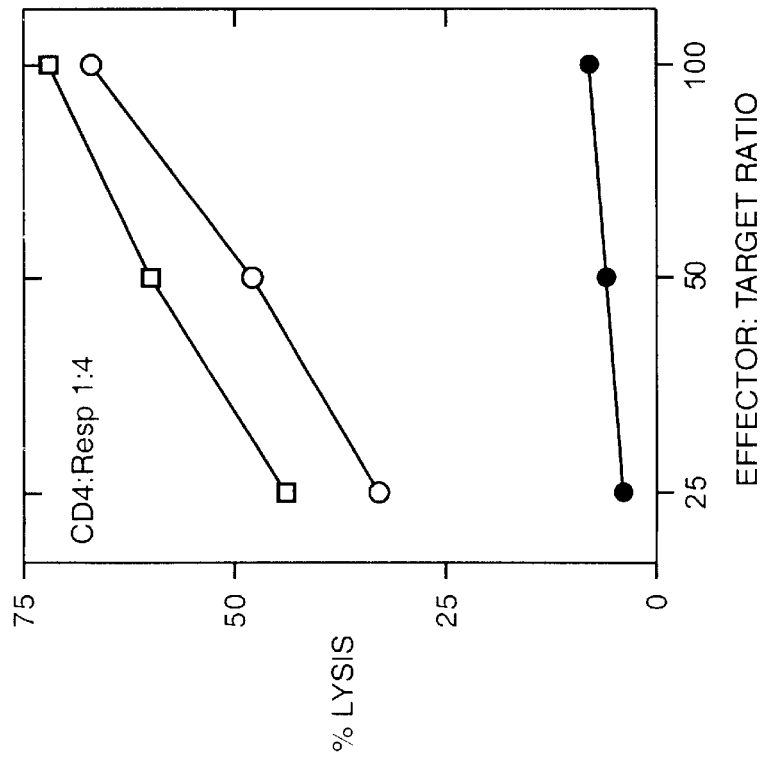
FIG._11A

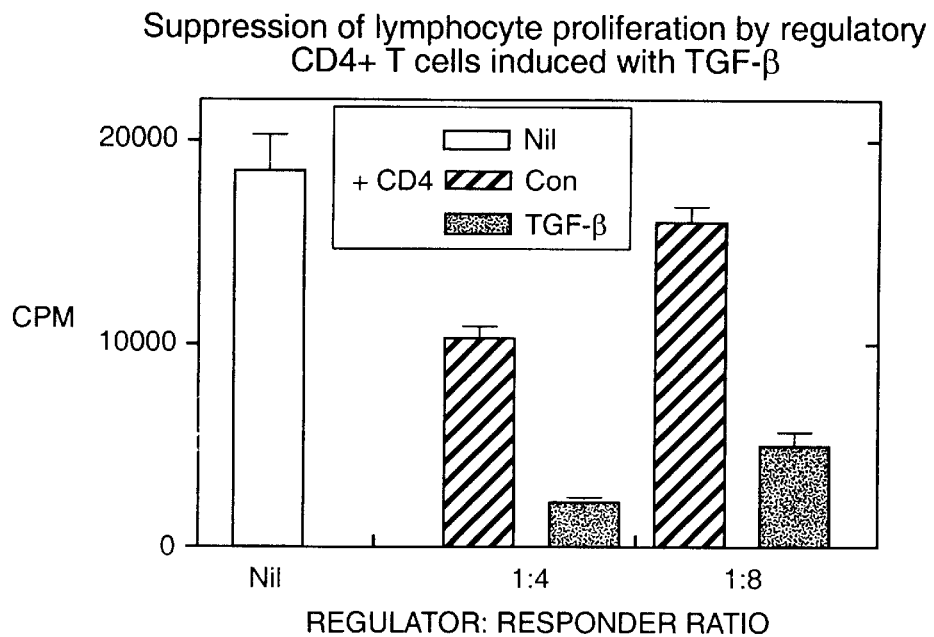
FIG._12
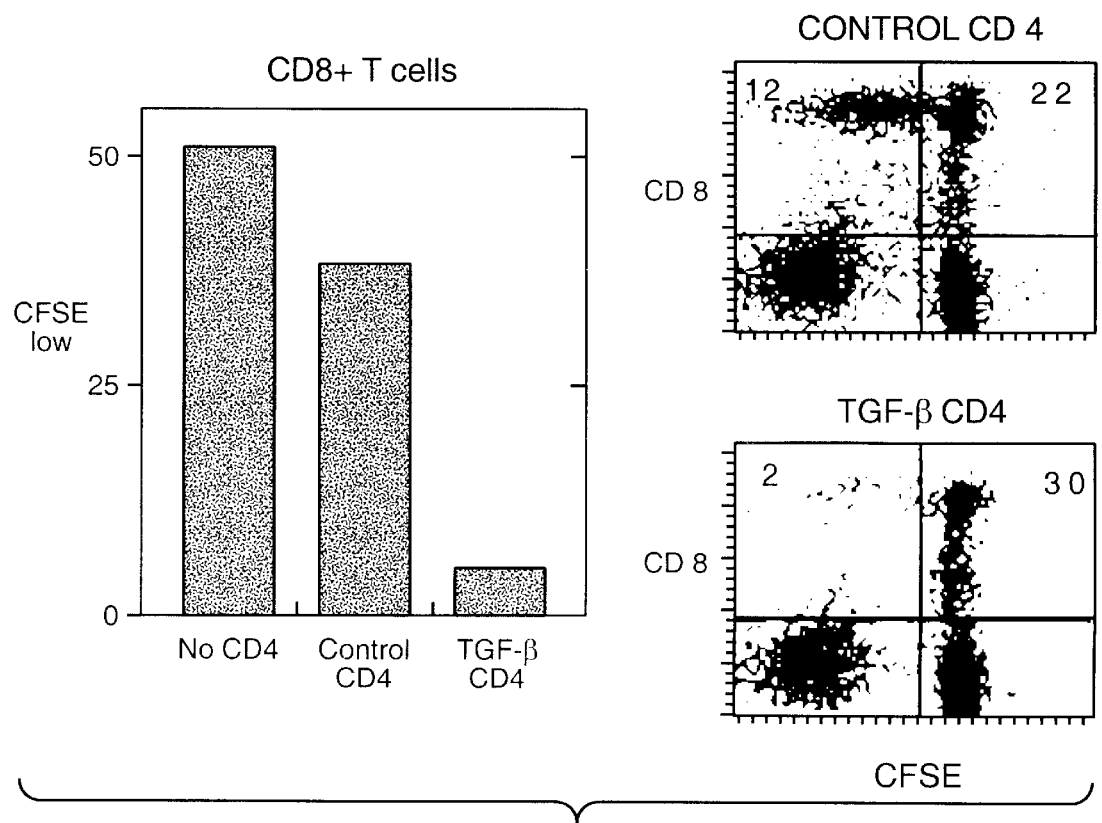
FIG._13

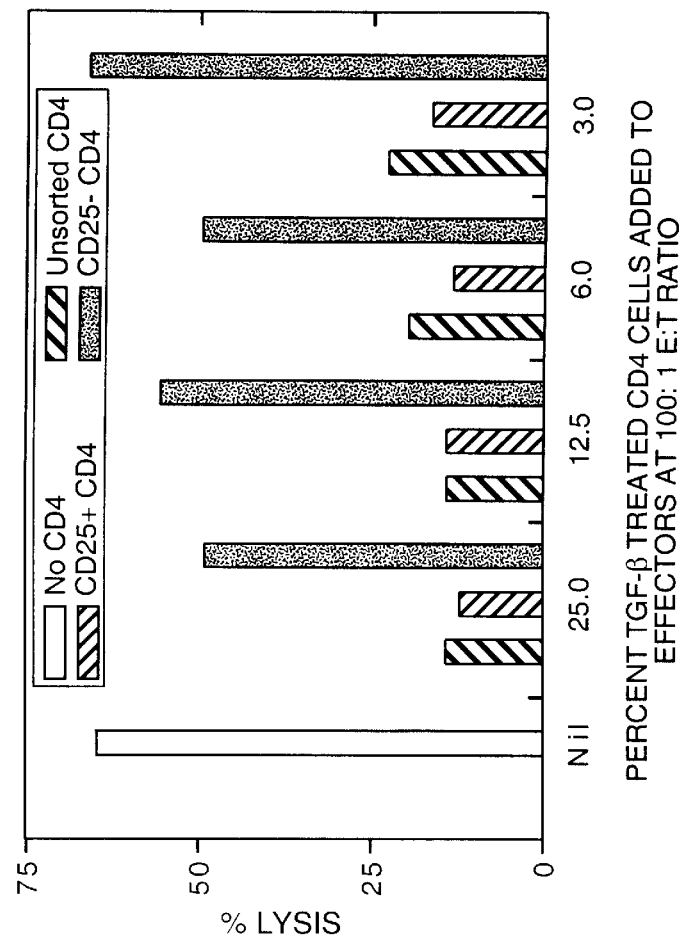
FIG._14B
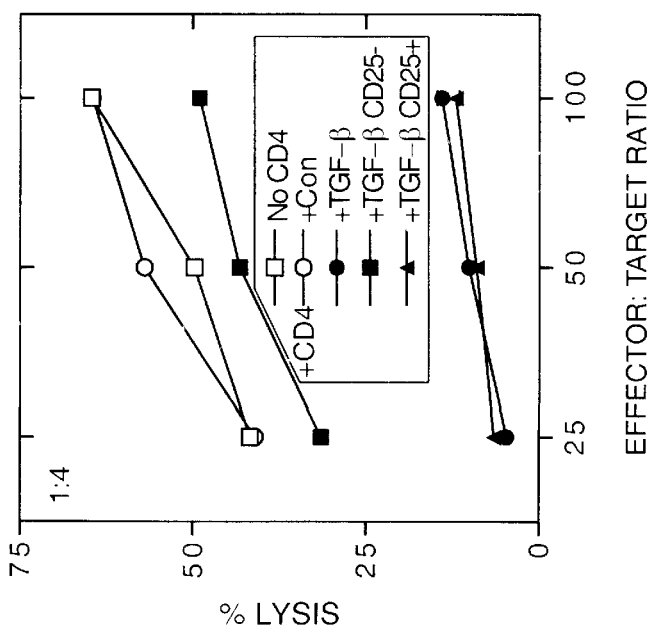
FIG._14A

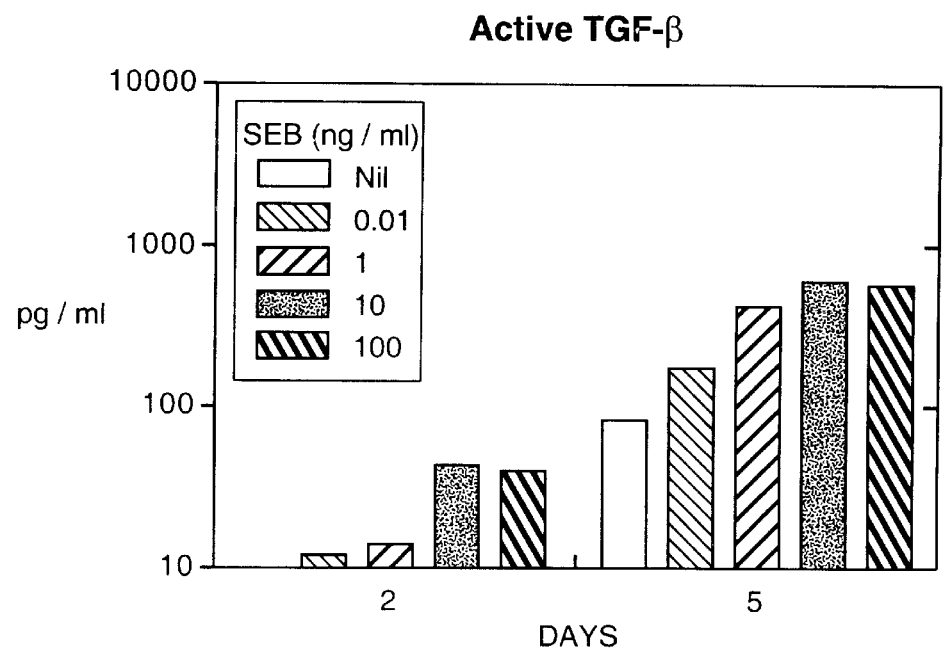
FIG._15A
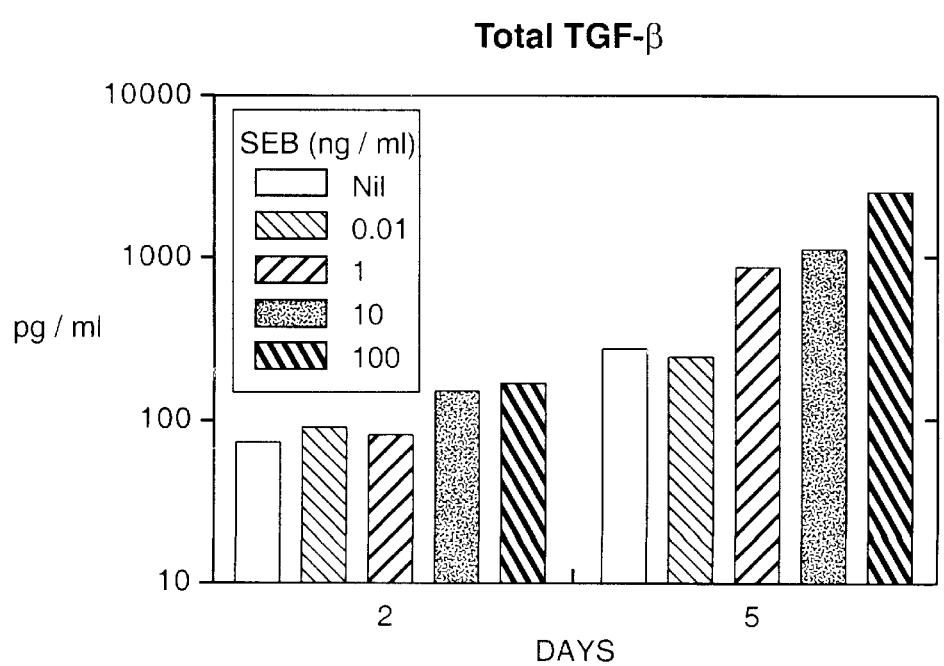
FIG._15B

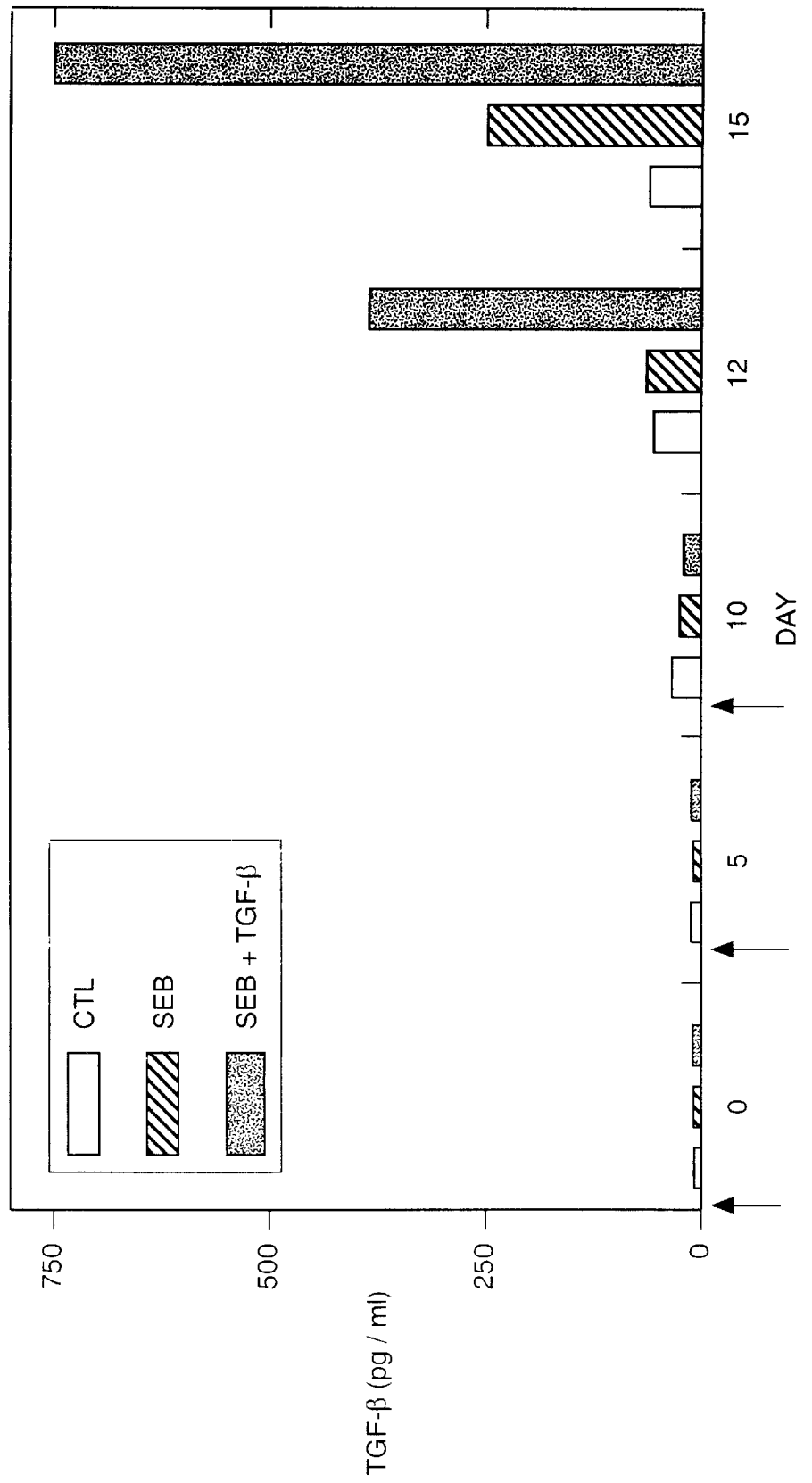
FIG._16

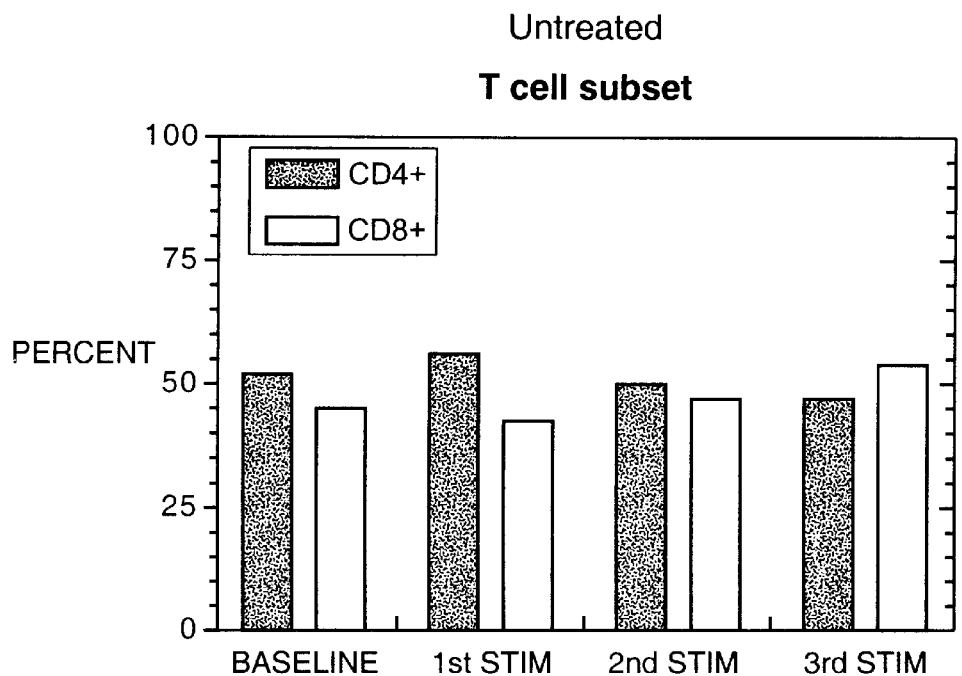
FIG._17A
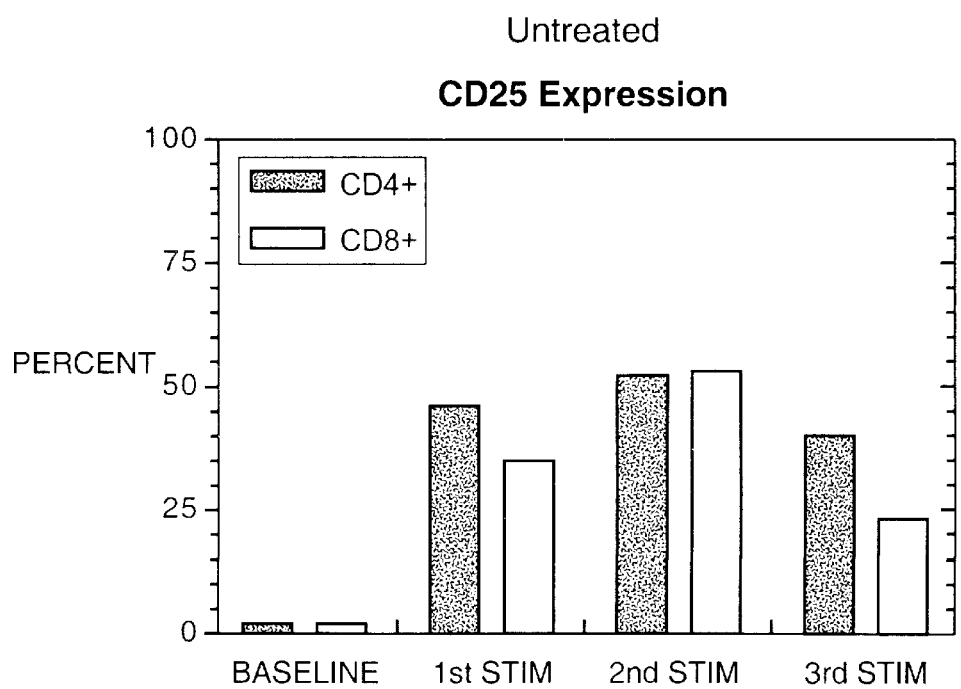
FIG._17B

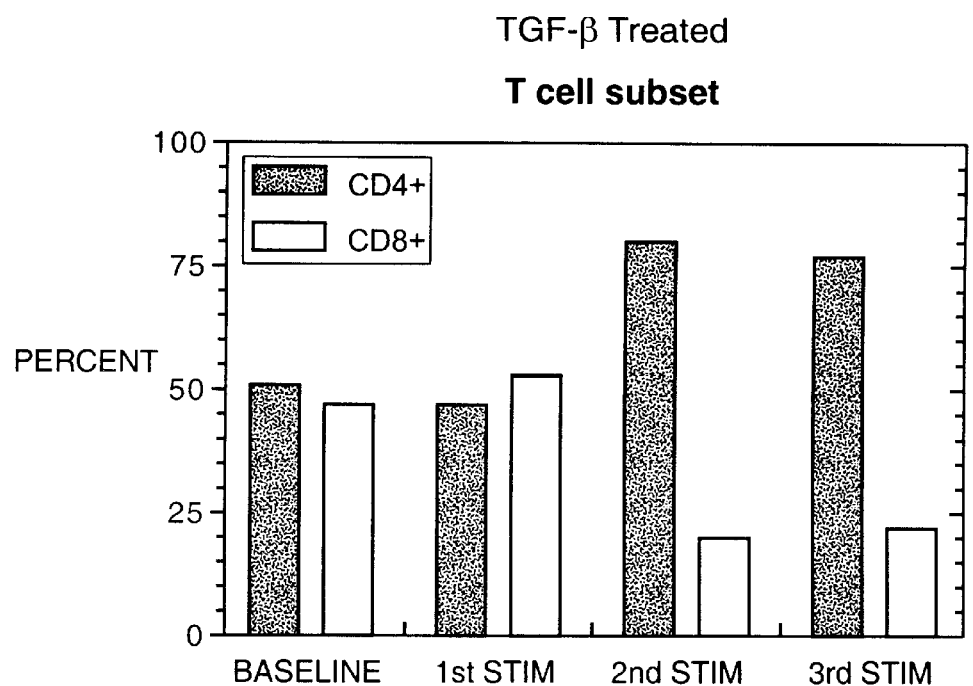
FIG._17C
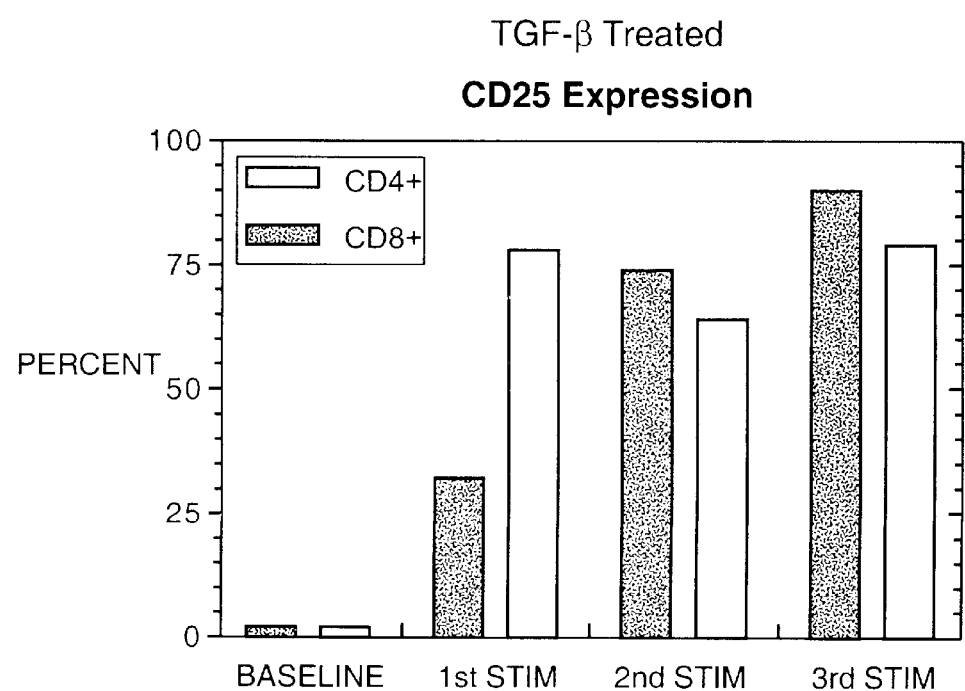
FIG._17D

USE OF CYTOKINES AND MITOGENS TO INHIBIT PATHOLOGICAL IMMUNE RESPONSES

This application is a continuing application of U.S. Ser. No. 09/564,436, filed May 4, 2000, now U.S. Pat. No. 6,358,506, which is a continuation in part of Ser. No. 09/186,771, filed Nov. 5, 1998, now U.S. Pat. No. 6,228, 359, and claims the benefit of the filing dates of U.S. Ser. No. 60/132,616, filed May 5, 1999 and Ser. No. 60/064,507, filed Nov. 5, 1997.

FIELD OF THE INVENTION

The field of the invention is generally related to methods of treating autoimmune diseases, including both antibody-mediated and cell-mediated disorders.

BACKGROUND OF THE INVENTION

Autoimmune diseases are caused by the failure of the immune system to distinguish self from non-self. In these diseases, the immune system reacts against self tissues and this response ultimately causes inflammation and tissue injury. Autoimmune diseases can be classified into two basic categories: antibody-mediated diseases such as systemic lupus erythematosus (SLE), pemphigus vulgaris, myasthenia gravis, hemolytic anemia, thrombocytopenia purpura, Grave's disease, Sjogren's disease and dermatomyositis; and cell-mediated diseases such as Hashimoto's disease, polymyositis, disease inflammatory bowel disease, multiple sclerosis, diabetes mellitus, rheumatoid arthritis, and scleroderma.

In many autoimmune diseases, tissue injury is caused by the production of antibodies to native tissue. These antibodies are called autoantibodies, in that they are produced by a mammal and have binding sites to the mammal's own tissue. Some of these disorders have characteristic waxing and waning of the amount of circulating autoantibodies causing varying symptoms over time.

Of the different types of antibody-mediated autoimmune disorders, SLE is a disorder that has been well studied and documented. SLE is a disorder of generalized autoimmunity characterized by B cell hyperactivity with numerous autoantibodies against nuclear, cytoplasmic and cell surface antigens. This autoimmune disease has a multifactorial pathogenesis with genetic and environmental precipitating factors (reviewed in Hahn, B. H., *Dubois' Lupus Erythematosus,* 5th Ed. (1997), pp. 69–76 (D. J. Wallace et al., eds., Williams and Wilkins, Baltimore)). Among the numerous lymphocyte defects described in SLE is a failure of regulatory T cells to inhibit B cell function (Horwitz, D. A., *Dubois' Lupus Erythematosus,* 5th Ed. (1997), pp. 155–194 (D. J. Wallace et al. eds., Williams and Wilkins, Baltimore)). Sustained production of polyclonal IgG and autoantibodies in vitro requires T cell help (Shivakumar, S. et al. (1989), *J Immunol* 143:103–112).

Regulatory T cells can down-regulate antibody synthesis by lytic or cytokine-mediated mechanisms. The latter involve transforming growth factor-beta (TGF-β) and other inhibitory cytokines (Wahl, S. M. (1994), *J Exp Med* 180:1587–190). Circulating B lymphocytes spontaneously secreting antibodies are increased in patients with active SLE (Klinman, D. M. et al., (1991), *Arthritis Rheum* 34:1404–1410).

Clinical manifestations of SLE include a rash (especially on the face in a "butterfly" distribution), glomerulonephritis, pleurisy, pericarditis and central nervous system involvement. Most patients are women, and are relatively young (average age at diagnosis is 29).

The treatment of SLE depends on the clinical manifestations. Some patients with mild clinical symptoms respond to simple measures such as nonsteroidal anti-inflammatory agents. However, more severe symptoms usually require steroids with potent anti-inflammatory and immunosuppressive action such as prednisone. Other strong immunosuppressive drugs which can be used are azathioprine and cyclophosphamide. The steroids and other immunosuppressive drugs have side effects due to the global reduction of the mammal's immune system. There is presently no ideal treatment for SLE and the disease cannot be cured.

Currently, considerable attention has been focused on the identity of genes which enhance the susceptibility or resistance to SLE, the identification of antigenic determinants that trigger the disease, the molecular mechanisms of T cell activation which results in survival or apoptosis, cytokines which determine T cell function, and the properties of the autoantibody-forming B cells. Many examples of T cell dysregulation in SLE have been described (reviewed in Horwitz, D. A. et al., *Dubois' Lupus Erythematosus,* 5th Ed. (1997), pp. 83–96 (D. J. Wallace et al. eds., Williams and Wilkins, Baltimore). Although it is well recognized that the primary role of certain lymphocytes is to down-regulate immune responses, progress in elucidating the identity and mechanisms required for generation of these cells has been slow.

Interleukin-2 (IL-2) has previously been considered to have an important role in the generation of antigen non-specific T suppressor cells. Anti-IL-2 antibodies given to mice coincident with the induction of graft-versus-host-disease resulted in several features of SLE (Via, C. S. et al. (1993), *International Immunol.* 5:565–572). Whether IL-2 directly or indirectly is important in the generation of suppression has been controversial (Fast, L. D. (1992), *J. Immunol.* 149:1510–1515; Hirohata, S. et al. (1989), *J. Immunol.* 142:3104–3112; Baylor, C. E. (1992), *Advances Exp. Med. Biol.* 319:125–135). Recently, IL-2 has been shown to induce CD8+ cells to suppress HIV replication in CD4+ T cells by a non-lytic mechanism. This effect is cytokine mediated, but the specific cytokine has not been identified (Kinter, A. L. et al. *Proc. Natl. Acad. Sci. USA* 92:10985–10989; Barker, T. D. et al. (1996), *J. Immunol.* 156:4478–4483). T cell production of IL-2 is decreased in SLE (Horwitz, D. A. et al. (1997), *Dubois' Lupus Erythematosus,* 5th Ed. (1997), pp. 83–96, D. J. Wallace et al. eds., Williams and Wilkins, Baltimore).

CD8+ T cells from subjects with SLE sustain rather than suppress polyclonal IgG production (Linker-Israeli, M. et al. (1990), *Arthritis Rheum.* 33:1216–1225). CD8+ T cells from healthy donors can be stimulated to enhance antibody production (Takahashi, T. et al. (1991), *Clin. Immunol. Immunopath.* 58:352–365). However, neither IL-2 nor CD4+ T cells, by themselves, were found to induce CD8+ T cells to develop strong suppressive activity. When NK cells were included in the cultures, strong suppressive activity appeared (Gray, J. D. et al. (1994) *J. Exp. Med.* 180:1937–1942). It is believed that the contribution of NK cells in the culture was to produce transforming growth factor beta (TGF-β) in its active form. It was then discovered that non-immunosuppressive (2–10 pg/ml) concentrations of this cytokine served as a co-factor for the generation of strong suppressive effects on IgG and IgM production (Gray, J. D. et al. (1994) *J. Exp. Med.* 180:1937–1942). In addition, it is believed that NK cells are the principal source of TGF-β in unstimulated lymphocytes (Gray, J. D. et al. (1998), *J. Immunol.* 160:2248–2254).

TGF-βs are a multifunctional family of cytokines important in tissue repair, inflammation and immunoregulation (Massague, J. (1980), *Ann. Rev. Cell Biol.* 6:597). TGF-β is unlike most other cytokines in that the protein released is biologically inactive and unable to bind to specific receptors (Sporn, M. B. et al. (1987) *J. Cell Biol.* 105:1039–1045). The latent complex is cleaved extracelluarly to release active cytokine as discussed below. The response to TGF-β requires the interaction of two surface receptors (TGF-β-R1) and TGF-β-R2) which are ubiquitously found on mononuclear cells (Massague, J. (1992), *Cell* 69:1067–1070). Thus, the conversion of latent to active TGF-β is the critical step which determines the biological effects of this cytokine.

It was found that SLE patients have decreased production of TGF-β1 by NK cells. Defects in constitutive TGF-β produced by NK cells, as well induced TGF-β were documented in a study of 38 SLE patients (Ohtsuka, K. et al. (1998), *J. Immunol.* 160:2539–2545). Neither addition of recombinant IL-2 or TNF-alpha, or antagonism of IL-10 normalized the TGF-β defect in SLE. Decreased production of TGF-β in SLE did not correlate with activity of disease and, therefore, may be a primary defect.

Systemic administration of TGF-β, IL-2, or a combination of both can lead to serious side effects. These cytokines have numerous effects on different body tissues and are not very safe to deliver to a patient systemically. It is, therefore, an object of the invention to provide methods and kits for treating mammalian cells that are responsible for controlling the regulation of autoantibodies to increase the population of cells that down regulate auto-antibody production.

SUMMARY OF THE INVENTION

In accordance with the objects outlined herein, the present invention provides methods for inhibiting immune responses in a sample of ex vivo peripheral blood mononuclear cells (PBMCs) comprising adding an regulatory composition to the cell population.

In an additional aspect, the present invention provides methods for treating an autoimmune disorder in a patient. The methods comprise removing peripheral blood mononuclear cells (PBMC) from the patient and treating the cells with an regulatory composition for a time sufficient to suppress inflamation and tissue injury. In particular, the methods of the present invention suppress antibody production or induce cells to down regulate antibody production and enhance cell mediated immune responses in patients with antibody mediated autoimmune diseases. The treated cells are then reintroduced to the patient, with a resulting amelioration of the autoimmune symptoms. The regulatory composition preferably comprises TGF-β and agents which enable T cells to respond to TGF-β.

In an additional aspect, the present invention provides methods for treating cell-mediated autoimmune diseases. The methods comprise removing peripheral blood mononuclear cells (PBMC) from the patient and treating the cells with an regulatory composition for a time sufficient to suppress tissue injury by immune cells. The treated cells are then reintroduced to the patient, with a resulting amelioration of the autoimmune symptoms. The regulatory composition preferably comprises TGF-β and agents which enable T cells to respond to TGF-β.

In an additional aspect, the invention provides kits for the treatment of an autoimmune disorder in a patient. The kits comprise a cell treatment container adapted to receive cells from a patient with an antibody-mediated autoimmune disorder or a cell-mediated disorder and at least one dose of an regulatory composition.

BRIEF DESCRIPTION OF THE DRAWINGS

FIG. 1 shows that incubation of SLE patients PBMC with IL-2 and TGF-β decreases spontaneous immunoglobulin production. PBMC ($2\times10^5$/well) were cultured in AIM-V serum free medium with or without IL-2 (10 U/ml) and TGF-β (10 pg/ml). After 3 days, the wells were washed three times and fresh AIM-V medium added. Supernatants were collected from the wells after a further 7 days and IgG content determined by an ELISA.

FIG. 2 shows that both IL-2 and TGF-β significantly decrease spontaneous IgG production. The values represent the mean±SEM of IgG (μg/ml) produced by the 12 SLE patients PBMC cultured as described in legend to FIG. 1 except some cells were also incubated with IL-2 (10 U/ml) or TGF-β (10 pg/ml) only.

FIGS. 3A and 3B show that anti-TGF-β can reverse the effects of IL-2. SLE patients PBMC was cultured for three days in the presence (solid bars) or absence (spotted bars) of IL-2 (10 U/ml). Included in these cultures was medium, anti-TGF-β (10 μg/ml) or control mouse IgG1 (10 μg/ml). After 3 days the wells were washed and fresh AIM-V medium added. Supernatants were collected after a further seven days and assayed for IgG (FIG. 3A) or antinucleoprotein (NP) (FIG. 3B) content by an ELISA.

FIGS. 4A, 4B and 4C depict regulatory effects of CD8+ T cells on antibody production. (A) Synergism between NK cells and CD8+ cells in the suppression of IgG production in a healthy subject. CD4+ cells and B cells were stimulated with anti-CD2 and the effects of CD8+ cells and NK cells were examined. The combination of NK and CD8+ cells markedly inhibited anti-CD2 induced IgG production we previously reported (Gray, J. D. et al. (1998), *J Immunol* 160:2248–2254; Gray, J. D. et al. (1994), *J Exp Med* 180:1937–1942). (B) NK cells and CD8+ cells enhance IgG synthesis in SLE. CD4+ cells from a patient with active SLE and resting B cells from a healthy subject were stimulated with anti-CD2. Enhancement of IgG production by SLE CD8+ cells was markedly increased by the addition of NK cells. (C) Cytokine normalization of CD8+ T cell function in SLE. In parallel with the study shown in FIG. 4B, CD4+ T cells from this patient were stimulated with anti-CD2 in the presence or absence of CD8+ T cells. IL-2 (10 U/ml) and/or TGF-β (2 pg/ml) was added where indicated. These cytokines abolished the helper effects of these CD8+ cells and enabled them to inhibit IgG production by 75%.

FIGS. 5A and 5B depict the lymphocyte production of TGF-β1 by unstimulated and anti-CD2 stimulated cells. PBL from healthy donors and patients of SLE and RA were added to microtiter plates at $1\times10^5$/well. Some wells received the anti-CD2 mAbs GT2 (1:40) and T11 (1:80). After 2 days at 37° C., supernatants were harvested and assayed for active and total TGF-β1. Significant p values are indicated.

FIG. 6 depicts the effects of TGF-β on T cell production of TNF-α and IL-10. Purified T cells ($1\times10^5$ cells/well) in serum free AIM V medium were added to flat bottomed microwells and stimulated with a low dose (0.5 μg/ml) or high dose (5 μg/ml) of Con A with or without IL-2 (10 U/ml) in the presence or absence of TGF-β (1 ng/ml). Supernatants were collected at 2 days and 5 days and tested for TNF-α and IL-10 by ELISA. Maximal production of TGF-β was found at 2 days and for IL-10 at 5 days. TGF-β abolished IL-10 production and up-regulated TNF-α production.

FIG. 7 shows that TNF-α is an essential intermediate for the generation of regulatory T cells by TGF-β. Purified CD8+ cells were incubated overnight with Con A (2.5

μg/ml), II-2 (10 U) and TGF-β (10 pg/ml). After washing these cells were added to CD4+ B cells and stimulated with anti-CD2. To some wells anti-TNF-α antibody (10 μg/ml) or isotype control antibody (10 μg/ml) was included. After 7 days, supernatants were evaluated for IgG content by an ELISA. The regulatory activity of conditioned CD8+ cells was reversed by anti-TNF-α.

FIG. 8 depicts that enhanced production of Th1 cytokines by TGF-β primed T cells is dependent upon TNF-α. Purifed naive T cells were cultured with Con A (5 μg/ml) an IL-2 (10 U/ml) in the presence of TGF-β (1 ng/ml). Some wells also received neutralizing anti-TNF-α antibody (10 μg/ml) or isotype control antibody (10 μg/ml). After 5 days of culture, the cells were washed and replated at $1 \times 10^5$ cells/well in fresh medium. The next day they were restimulated with Con A and IL-2 for 6 hours and, in the presence of brefeldin A (10 μg/ml), the cells were stained for CD8 and the cytokines indicated. The percentage of CD8+ and CD8– cells expressing TNF-α, IL-2 and IFN-γ is shown. Note that neutralization of TNF-α in primary cultures abolished the enhancing effects of TGF-β on production of Th1 cytokines.

FIG. 9 depicts the effect of TGF-β in generating suppressors of cytotoxic T cell activity. T cells from donor A prepared by E rosetting were divided into two portions. One portion was used as responders for an allogeneic mixed lymphocyte reaction (allo-MLR). The other portion was used to prepare the T cell subsets indicated by negative selection after staining the cells with appropriate monoclonal antibodies and removing the stained cells using immunomagnetic beads. The responder T cells were mixed with stimulator cells from donor B (irradiated T cell depleted peripheral blood mononuclear cells) and cultured for 5 days to generate killer cells. Contols consisted of the T cell subsets cultured for 5 days with or without stimulator cells. Afterwards, the cells were washed, counted and used to assess allo-cytotoxic T cell activity. The responder cells from donor A were mixed with chromium labeled lymphoblasts from donor B in the effector to target cell ratios shown and chromium release was measured in a standard 4 hour assay (open squares). T cells subsets cultured with stimulators were added in a ratio of 1 regulatory cell per 4 responder cells (open circles). T cell subsets cultured with stimulators with TGF-beta are shown as closed circles. In all experiments, the maximal effects of TGF-beta were on naive CD4 CD45RA+ CD45RO– cells.

FIG. 10 depicts the effect of CD4 cells primed with TGF-beta on allo-cytotoxic T lymphocyte (CTL) activity. The addition of CD4 CD45RA cells that had been cultured for 5 days without stimulators had no effect on CTL activity (result not shown). Culturing these T cells with stimulator cells resulted in modest to moderate suppressive activity. In all experiments, culture of these T cells with TGF-beta 1 ng/ml markedly suppressed, or abolished allo-CTL activity.

FIG. 11 demonstrates that regulatory T cells require cell contact to inhibit CTL activity. Regulatory CD4 cells were prepared from CD4 CD45RA cells cultured with TGF-beta as described above. Some of these cells were mixed with responder and chromium-labeled target cells, while others were separated from the killer cells by a membrane. Inhibition of cytotoxic T lymphocyte activity (CTL) was only observed when the regulatory T cells were in direct contact with the killer cells.

FIG. 12 depicts suppression of lymphocyte proliferation by regulatory CD4+ T cells induced with TGF-β. Naïve CD4+ T cells from donor A were mixed with stimulator cells as described above and added to fresh responder and stimulator cells at the indicated ratios. The bars show the uptake of tritiated thymidine±SEM after 7 days of culture. The lightly shaded bar (Nil) indicates the proliferative response of the responder T cells without added CD4+ cells. The darkly shaded bar indicates the effect of control CD4+ cells which had been cultured with stimulator cells without TGF-β. The black bar indicates the effect of CD4+ cells that had been mixed with stimulator cells in the presence of TGF-β (1 ng/ml). The effect of these CD4+ cells on the proliferative response of fresh responder cells added to irradiated stimulator cells after 7 days of culture is shown. The bars indicate the mean uptake of tritiated thymidine.

FIG. 13 depicts the regulatory activity of CD25+ CD4 T cells. CD4+ cells were stimulated with irradiated allogeneic non-T cells±TGF-β (1 ng/ml) for 5 days. After washing, the CD4+ cells were stained with DII and fresh responder T cells were stained with carboxyfluorescein (CFSE). control or TGF-β primed CD4+ cells were added to the responder T cells and allo-stimulator cells in a 1:4 ratio. After 5 days, the cells were harvested and analyzed by flow cytometry. The intensity of CFSE in CD8+ cells was determined by gating on DII negative cells. Note that the addition of TGF-β primed CD4+ cells to responder T cells markedly decreased cell division by CD8+ cells.

FIG. 14 depicts that regulatory CD4+ cells express CD25+ (IL-2) receptors on their surface. Control and TGF-β induced CD4+ regulatory T cells were prepared as described above. After conditioning with allo-stimulator cells and TGF-β, the CD4+ cells were divided into CD25+ and CD25– subsets by cell sorting and added to fresh responder T cells and irradiated stimulator cells. The capacity of these responder cells to kill stimulator T lymphoblasts is shown in a standard 4 hour chromium release assay.

In FIG. 14A, the open boxes show CTL activity without additional CD4+ cells. Control or TGF-β induced regulatory T cells were added in a 1:4 ratio with responder cells. The open circles show that the control CD4+ cells did not alter CTL activity. The solid circles show that TGF-β induced CD4+ cells almost completely suppressed CTL activity. The solid diamonds show that the suppressive activity was contained exclusively in the CD25+ subset. The CD25– subset (solid squares) did not have suppressive activity.

FIG. 14B shows the effect of decreasing the numbers of CD4+ regulatory cells added to the MLR. Decreasing the number to only 3% had a minimal effect in decreasing the suppressive effects.

FIG. 15 depicts that repeated stimulation of T cells with a low dose of staphylococcal enterotoxin B (SEB) induces T cells to produce immunosuppressive levels of TGF-β. CD4+ T cells were stimulated with SEB (0.01 ng/ml) and irradiated B cells as superantigen presenting cells with our without TGF-β at the times indicated by the arrows. Active TGF-β was measured 2 or 5 days later.

FIG. 16 depicts that repeated stimulation of CD4+ T cells with a low dose of SEB enables these cells to produce immunosuppressive levels of TGF-β. CD4+ T cells were stimulated with SEB (0.01 ng/ml) and irradiated B cells as superantigen presenting cells with or without TGF-β at the times indicated by the arrows. Active TGF-β was measured 2 or 5 days later.

FIG. 17 shows the effects of SEB on naive (CD45RA+ CD45RO–) CD4+ and CD8+ T cells. The cells were stimulated with SEB every 5th day for a total of three stimulations. The percentages of each T cell subset and the cells expressing the CD25 IL-2 receptor activation marker were determined after each stimulation. Panels A and C show that if TGF-β 1 ng/ml was included in the initial stimulation, CD4+ T cells became the predominant subset in the cultures after repeated stimulation. Panels B and D show that CD25 expression by SEB stimulated cells decreases by the third stimulation in control cultures. However, CD25 expression remains high if the T cells have been primed with TGF-β.

DETAILED DESCRIPTION

The present invention is directed to methods of treating autoimmune disorders, including both cell-mediated and antibody-mediated disorders such as systemic lupus erythematosus (SLE). The methods involve removing cells from a patient and treating them with a composition that can act in one of two ways. In one embodiment, symptoms of antibody-mediated autoimmune disorders are ameliorated using the compositions of the invention. The compositions down-regulates B cell hyperactivity thereby inhibiting the production of antibodies, including autoantibodies,. In addition, the compositions enhance cell mediated immune responses that are frequently defective in patients with SLE and certain other antibody-mediated autoimmune disorders; that is, patients with antibody-mediated autoimmune disorders can be treated to ameliorate their defective cell-mediated symptoms.

Alternatively, the compositions are used to treat cell-mediated autoimmune disease. In this embodiment, the compositions induce immune cells to generate suppressor T cells. These suppressor T cells prevent other T cells from becoming cytotoxic and attacking the cells and tissue of an affected individual. Thus, the composition decrease cytotoxicity and thereby ameliorate the symptoms of cell-mediated autoimmune disorders.

This strategy is unlike almost all other treatment modalities currently in use which are either anti-inflammatory or immunosuppressive. Commonly used corticosteroids suppress cytokine production and block the terminal events which cause tissue injury, but generally do not alter the underlying autoimmune response. Cytotoxic drugs or experimental genetically engineered biologicals such as monoclonal antibodies may also deplete specific lymphocyte populations or interfere with their function. These drugs are generally only moderately successful and have severe adverse side effects. Certain cytokines have been given systemically to patients, but these agents also have broad actions with associated serious adverse side effects.

By contrast, the strategy of the present invention is to produce remission by restoring normal regulatory cell function and, thus, "resetting" the immune system. Another significant potential advantage of this strategy is a low probability of serious adverse side effects. Since only trace amounts of regulatory compositions such as cytokines will be returned to the patient, there should be minimal toxicity.

Circulating B lymphocytes spontaneously secreting IgG are increased in patients with active SLE (Blaese, R. M., et al. (1980), *Am J. Med* 69:345–350; Klinman, D. M. et al. (1991) *Arthritis Rheum* 34: 1404–1410). Sustained production of polyclonal IgG and autoantibodies in vitro requires T cell help (Shivakumar, S. et al. (1989), *J Immunol* 143:103–112). Previous studies of T cell regulation of spontaneous IgG production shows that while CD8+ T cells inhibit antibody production in healthy individuals, in SLE these cells support B cell function instead (Linker-Israeli, M. et al. (1990), *Arthritis Rheum* 33:1216–1225). In other autoimmune diseases such as rheumatoid arthritis and multiple sclerosis, T cells rather than antibody are responsible for tissue injury and the resulting inflammation (Panayi G S, et al. Arthritis Rheum (1992) 35:725–773), Allegretta M et al. Science (1990) 247:718–722.

Accordingly, in a preferred embodiment, the present invention is drawn to methods of treating antibody- and T cell-mediated autoimmune diseases that comprise removing peripheral blood mononuclear cells (PBMCs) from the patient with the autoimmune disease and treating certain of these cells with an regulatory composition.

Without being bound by theory, it appears there are several ways the methods of the invention may work. First of all, the treatment of the cells by an regulatory composition leads to the direct suppression of antibody production in the treated cells, which can lead to amelioration of antibody-mediated autoimmune symptoms. Alternatively or additionally, the treatment of the cells induces regulatory cells to down regulate antibody production in other cells. Antibody in this context includes all forms of antibody, including IgA, IgM, IgG, IgE, etc. The net result is a decrease in the amount of antibody in the system.

Additionally, the treatment of the cells enhances cell-mediated immune responses in patients with antibody-mediated autoimmune symptoms. Without being bound by theory, it appears that the treatment of the cells restores the balance between IL-10 and TNF-α leading to an enhanced production of Th1 cytokines and normalization of cell mediated immunity.

Furthermore, stimulation of immune cells with regulatory compositions including TGF-β can suppress cell-mediated immune responses. Without being bound by theory, it appears that CD4+ T cells can be stimulated to produce immunosuppressive levels of active TGF-β, that then suppresses cell-mediated immune responses. Alternatively, CD4+ T cells can be stimulated to suppress the activation and/or effector functions of other T cells by a contact-dependent mechanism of action. These effects require CD4+ cells to be activated in the presence of TGF-β.

Thus, the present invention inhibits aberrant immune responses. In patients with antibody-mediated autoimmune disorders, the present invention restores the capacity of peripheral blood T cells to down regulate antibody production and restores cell mediated immune responses by treating them with an regulatory composition ex vivo. In patients with cell-mediated disorders, the present invention generates regulatory T cells which suppress cytotoxic T cell activity in other T cells.

By "immune response" herein is meant host responses to foreign or self antigens. By "aberrant immune responses" herein is meant the failure of the immune system to distinguish self from non-self or the failure to respond to foreign antigens. In other words, aberrant immune responses are inappropriately regulated immune responses that lead to patient symptoms. By "inappropriately regulated" herein is meant inappropriately induced, inappropriately suppressed and/or non-responsiveness. Aberrant immune responses include, but are not limited to, tissue injury and inflammation caused by the production of antibodies to an organism's own tissue, impaired production of IL-2, TNF-α and IFN-γ and tissue damage caused by cytotoxic or non-cytotoxic mechanisms of action.

Accordingly, in a preferred embodiment, the present invention provides methods of treating antibody-mediated autoimmune disorders in a patient. By "antibody-mediated autoimmune diseases" herein is meant a disease in which individuals develop antibodies to constituents of their own cells or tissues. Antibody-mediated autoimmune diseases include, but are not limited to, systemic lupus erythematosus (SLE), pemphigus vulgaris, myasthenia gravis, hemolytic anemia, thrombocytopenia purpura, Grave's disease, dermatomyositis and Sjogren's disease. The preferred autoimmune disease for treatment using the methods of the invention is SLE.

In addition, patients with antibody-mediated disorders frequently have defects in cell-mediated immune responses. By "defects in cell mediated immune response" herein is meant impaired host defense against infection. Impaired host defense against infection includes, but is not limited to, impaired delayed hypersensitivity, impaired T cell cytotoxicity and impaired production of TGF-β. Other defects, include, but are not limited to, increased production of IL-10 and decreased production of IL-2, TNF-α and IFN-γ. Using the methods of the present invention, purified T cells are stimulated to increase production of IL-2, TNF-α and IFN-γ and decrease production of IL-10. T cells which can be stimulated using the current methods include, but are not limited to, CD4+ and CD8+.

In one embodiment, antibody-mediated disorders are not treated.

In a preferred embodiment, the present invention provides methods of treating cell-mediated autoimmune disorders in a patient. By "cell-mediated autoimmune diseases" herein is meant a disease in which the cells of an individual are activated or stimulated to become cytotoxic and attack their own cells or tissues. Alternatively, the autoimmune cells of the individual may stimulate other cells to cause tissue damage by cytotoxic or non-cytotoxic mechanisms of action. Cell-mediated autoimmune diseases include, but are not limited to, Hashimoto's disease, polymyositis, disease inflammatory bowel disease, multiple sclerosis, diabetes mellitus, rheumatoid arthritis, and scleroderma.

By "treating" an autoimmune disorder herein is meant that at least one symptom of the autoimmune disorder is ameliorated by the methods outlined herein. This may be evaluated in a number of ways, including both objective and subjective factors on the part of the patient. For example, immunological manifestations of disease can be evaluated; for example, the level of spontaneous antibody and autoantibody production, particularly IgG production in the case of SLE, is reduced. Total antibody levels may be measured, or autoantibodies, including, but not limited to, anti-double-stranded DNA (ds DNA) antibodies, anti-nucleoprotein antibodies, anti-Sm, anti-Rho, and anti-La. Cytotoxic activity can be evaluated as outlined herein. Physical symptoms may be altered, such as the disappearance or reduction in a rash in SLE. Renal function tests may be performed to determine alterations; laboratory evidence of tissue damage relating to inflammation may be evaluated. Decreased levels of circulating immune complexes and levels of serum complement are further evidence of improvement. In the case of SLE, a lessening of anemia may be seen. The ability to decrease a patient's otherwise required drugs such as immunosuppressives can also be an indication of successful treatment. Other evaluations of successful treatment will be apparent to those of skill in the art of the particular autoimmune disease.

By "patient" herein is meant a mammalian subject to be treated, with human patients being preferred. In some cases, the methods of the invention find use in experimental animals, in veterinary application, and in the development of animal models for disease, including, but not limited to, rodents including mice, rats, and hamsters; and primates.

The methods provide for the removal of blood cells from a patient. In general, peripheral blood mononuclear cells (PBMCs) are taken from a patient using standard techniques. By "peripheral blood mononuclear cells" or "PBMCs" herein is meant lymphocytes (including T-cells, B-cells, NK cells, etc.) and monocytes. As outlined more fully below, it appears that in one embodiment, the main effect of the regulatory composition is to enable CD8+ or CD4+ T lymphocytes to suppress harmful autoimmune responses. Accordingly, the PBMC population should comprise CD8+ T cells. Preferably, only PBMCs are taken, either leaving or returning substantially all of the red blood cells and polymorphonuclear leukocytes to the patient. This is done as is known in the art, for example using leukophoresis techniques. In general, a 5 to 7 liter leukophoresis step is done, which essentially removes PBMCs from a patient, returning the remaining blood components. Collection of the cell sample is preferably done in the presence of an anticoagulant such as heparin, as is known in the art.

In some embodiments, a leukophoresis step is not required.

In general, the sample comprising the PBMCs can be pretreated in a wide variety of ways. Generally, once collected, the cells can be additionally concentrated, if this was not done simultaneously with collection or to further purify and/or concentrate the cells. The cells may be washed, counted, and resuspended in buffer.

The PBMCs are generally concentrated for treatment, using standard techniques in the art. In a preferred embodiment, the leukophoresis collection step results a concentrated sample of PBMCs, in a sterile leukopak, that may contain reagents and/or doses of the regulatory composition, as is more fully outlined below. Generally, an additional concentration/purification step is done, such as Ficoll-Hypaque density gradient centrifugation as is known in the art.

In a preferred embodiment, the PBMCs are then washed to remove serum proteins and soluble blood components, such as autoantibodies, inhibitors, etc., using techniques well known in the art. Generally, this involves addition of physiological media or buffer, followed by centrifugation. This may be repeated as necessary. They can be resuspended in physiological media, preferably AIM-V serum free medium (Life Technologies) (since serum contains significant amounts of inhibitors) although buffers such as Hanks balanced salt solution (HBBS) or physiological buffered saline (PBS) can also be used.

Generally, the cells are then counted; in general from $1 \times 10^9$ to $2 \times 10^9$ white blood cells are collected from a 5–7 liter leukophoresis step. These cells are brought up roughly 200 mls of buffer or media.

In a preferred embodiment, the PBMCs may be enriched for one or more cell types. For example, the PBMCs may be enriched for CD8+ T cells or CD4+ T cells. This is done as is known in the art, as described in Gray et al. (1998), *J. Immunol.* 160:2248, hereby incorporated by reference. Generally, this is done using commercially available immunoabsorbent columns, or using research procedures (the PBMCs are added to a nylon wool column and the eluted, nonadherent cells are treated with antibodies to CD4, CD16, CD11b and CD74, followed by treatment with immunomagnetic beads, leaving a population enriched for CD8+ T cells).

In a preferred embodiment, the PBMCs are separated in a automated, closed system such as the Nexell Isolex 300i Magnetic Cell Selection System. Generally, this is done to maintain sterility and to insure standardization of the methodology used for cell separation, activation and development of suppressor cell function.

Once the cells have undergone any necessary pretreatment, the cells are treated with an regulatory composition. By "treated" herein is meant that the cells are incubated with the regulatory composition for a time period sufficient to develop the capacity to inhibit immune responses, including antibody and autoantibody production, particularly when transferred back to the patient. The incubation will generally be under physiological temperature. As noted above, this may happen as a result of direct suppression of Antibody production by the treated cells, or by inducing regulatory cells to down regulate the production of antibody in the patient's lymphoid organs.

By "regulatory composition" or "antibody production inhibitor composition" or "humoral inhibitor composition" or "non-specific immune cell inhibitor" or specific T cell inhibitor" or "inhibitory composition" or "suppressive composition" herein is meant a composition that can cause suppression of immune responses, including inhibition of T cell activation, inhibition of spontaneous antibody and autoantibody production, or cytotoxicity, or both. Generally, these compositions are cytokines. Suitable regulatory compositions include, but are not limited to, T cell activators such as anti-CD2, including anti-CD2 antibodies and the CD2 ligand, LFA-3, and mixtures or combinations of T cell activators such as Concanavalin A (Con A), staphylococcus enterotoxin B (SEB), anti-CD3, anti-CD28 and cytokines such as IL-2, IL-4, TGF-$\beta$ and TNF-$\alpha$. A preferred regulatory composition for antibody suppression is a mixture containing a T cell activator, IL-2 and TGF-$\beta$. The preferred regulatory composition for suppression of cytotoxicity is TGF-$\beta$.

The concentration of the regulatory composition will vary on the identity of the composition. In a preferred embodiment, TFG-$\beta$ is a component the regulatory composition. By "transforming growth factor-$\beta$" or "TGF-$\beta$" herein is meant any one of the family of the TGF-$\beta$s, including the three isoforms TGF-$\beta$1, TGF-$\beta$2, and TGF-$\beta$3; see Massague, J. (1980), *J. Ann. Rev. Cell Biol* 6:597. Lymphocytes and monocytes produce the $\beta$1 isoform of this cytokine (Kehrl, J. H. et al. (1991), *Int J Cell Cloning* 9: 438–450). The TFG-$\beta$ can be any form of TFG-$\beta$ that is active on the mammalian cells being treated.

In humans, recombinant TFG-$\beta$ is currently preferred. A preferred human TGF-$\beta$ can be purchased from Genzyme Pharmaceuticals, Farmington, Mass. In general, the concentration of TGF-$\beta$ used ranges from about 2 picograms/ml of cell suspension to about 5 nanograms, with from about 10 pg to about 4 ng being preferred, and from about 100 pg to about 2 ng being especially preferred, and 1 ng/ml being ideal.

In a preferred embodiment, IL-2 is used in the regulatory composition. The IL-2 can be any form of IL-2 that is active on the mammalian cells being treated. In humans, recombinant IL-2 is currently preferred. Recombinant human IL-2 can be purchased from Cetus, Emeryville, Calif. In general, the concentration of IL-2 used ranges from about 1 Unit/ml of cell suspension to about 100 U/ml, with from about 5 U/ml to about 25 U/ml being preferred, and with 10 U/ml being especially preferred. In a preferred embodiment, IL-2 is not used alone.

In a preferred embodiment, CD2 activators, such as a combination of mitogenic anti CD2 antibodies, which may include the CD2 ligand LFA-3, are used as the regulatory composition. CD2 is a cell surface glycoprotein expressed by T lymphocytes. By "CD2 activator" herein is meant compound that will initiate the CD2 signaling pathway. A preferred CD2 activator comprises anti CD2 antibodies (OKT11, American Type Culture Collection, Rockville Md. and GT2, Huets, et al., (1986) J. Immunol. 137:1420). In general, the concentration of CD2 activator used will be sufficient to induce the production of TGF-$\beta$. The concentration of anti CD2 antibodies used ranges from about 1 ng/ml to about 10 $\mu$g/ml, with from about 10 ng/ml to about 100 ng/ml being especially preferred.

In some embodiments it is desirable to use a mitogen to activate the cells; that is, many resting phase cells do not contain large amounts of cytokine receptors. The use of a mitogen such as Concanavalin A or staphylococcus enterotoxin B (SEB) can allow the stimulation of the cells to produce cytokine receptors, which in turn makes the methods of the invention more effective. When a mitogen is used, it is generally used as is known in the art, at concentrations ranging from 1 $\mu$g/ml to about 10 $\mu$g/ml is used. In addition, it may be desirable to wash the cells with components to remove the mitogen, such as $\alpha$-methyl mannoside, as is known in the art.

In a preferred embodiment, T cells are strongly stimulated with mitogens, such as anti-CD2, anti-CD3, anti-CD28 or combinations of monoclonal antibodies, or a specific autoantigen, if known, and anti-CD28 or IL-2 as a co-stimulator. ConA is also used to stimulate T cells. The presence of TGF-$\beta$ in the suppressive composition induces T cells to develop potent suppressive activity. Repeated stimulation of the T cells with our without TGF-$\beta$ in secondary cultures may be necessary to develop maximal suppressive activity.

In a preferred embodiment, the invention provides methods comprising conditioning T cells, including, but not limited to CD8+ T or CD4+ T cells, and other minor T cell subsets such as CD8$^-$CD4$^-$, TandK, etc., with TGF-$\beta$. These T cells prevent other T cells from becoming cytotoxic effector cells.

In a preferred embodiment, the invention provides methods comprising conditioning CD4+ or CD8+ T cells with TGF-$\beta$ to produce immunosuppresive levels of TGF-$\beta$.

In a preferred embodiment, the invention provides methods comprising conditioning CD4+ or CD8+ T cells with TGF-$\beta$ to produce T cells that suppress by a contact-dependent mechanism.

In a preferred embodiment, the invention provides methods comprising treating naive CD4+ T cells with a stimulant such that said CD4+ cells produce immunosuppressive levels of active TGF-$\beta$. By "stimulant" is generally meant a generalized stimulant that triggers all T cells, such as anti-CD2 or anti-CD3.

In a preferred embodiment, the invention provides methods comprising stimulating naive CD4+ T cells in the presence of TGF-$\beta$ to expand the CD4+ cell population.

In a preferred embodiment, the invention provides methods which decrease production of IL-10 and correspondingly increase TNF-$\alpha$ production.

The regulatory composition is incubated with the cells for a period of time sufficient to cause an effect. In a preferred embodiment, treatment of the cells with the regulatory composition is followed by immediate transplantation back into the patient. Accordingly, in a preferred embodiment, the cells are incubated with the regulatory composition for 12 hours to about 7 days. The time will vary with the suppressive activity desired. For suppression of antibody production 48 hours is especially preferred and 5 days is especially preferred for suppression of cytotoxicity.

In one embodiment, the cells are treated for a period of time, washed to remove the regulatory composition, and may be reincubated to expand the cells. Before introduction into the patient, the cells are preferably washed as outlined herein to remove the regulatory composition. Further incubations for testing or evaluation may also be done, ranging in time from a few hours to several days. If evaluation of antibody production prior to introduction to a patient is desirable, the cells will be incubated for several days to allow antibody production (or lack thereof) to occur.

Once the cells have been treated, they may be evaluated or tested prior to autotransplantation back into the patient. For example, a sample may be removed to do: sterility testing; gram staining, microbiological studies; LAL studies; mycoplasma studies; flow cytometry to identify cell types; functional studies, etc. Similarly, these and other lymphocyte studies may be done both before and after treatment.

In a preferred embodiment, the quantity or quality, i.e. type, of antibody production, may be evaluated. Thus, for example, total levels of antibody may be evaluated, or levels of specific types of antibodies, for example, IgA, IgG, IgM, anti-DNA autoantibodies, anti-nucleoprotein (NP) antibodies, etc. may be evaluated. Regulatory T cells may also be assessed for their ability to suppress T cell activation or to prevent T cell cytotoxicity against specific target cells in vitro.

In a preferred embodiment, the levels of antibody, particularly IgG, are tested using well known techniques, including ELISA assays, as described in Abo et al. (1987), Clin. Exp. Immunol. 67:544 and Linker-Israeli et al. (1990), Arthritis Rheum 33:1216, both of which are hereby expressly incorporated by reference. These techniques may also be used to detect the levels of specific antibodies, such as autoantibodies.

In a preferred embodiment, the treatment results in a significant decrease in the amount of IgG and autoantibodies produced, with a decrease of at least 10% being preferred, at least 25% being especially preferred, and at least 50% being particularly preferred. In many embodiments, decreases of 75% or greater are seen.

In a preferred embodiment, prior to transplantation, the amount of total or active TGF-β can also be tested. As noted herein, TGF-β is made as a latent precursor that is activated post-translationally.

After the treatment, the cells are transplanted or reintroduced back into the patient. This is generally done as is known in the art, and usually comprises injecting or introducing the treated cells back into the patient, via intravenous administration, as will be appreciated by those in the art. For example, the cells may be placed in a 50 ml Fenwall infusion bag by injection using sterile syringes or other sterile transfer mechanisms. The cells can then be immediately infused via IV administration over a period of time, such as 15 minutes, into a free flow IV line into the patient. In some embodiments, additional reagents such as buffers or salts may be added as well.

After reintroducing the cells into the patient, the effect of the treatment may be evaluated, if desired, as is generally outlined above. Thus, evaluating immunological manifestations of the disease may be done; for example the titers of total antibody or of specific immunoglobulins, renal function tests, tissue damage evaluation, etc. may be done. Tests of T cells function such as T cell numbers, phenotype, activation state and ability to respond to antigens and/or mitogens also may be done.

The treatment may be repeated as needed or required. For example, the treatment may be done once a week for a period of weeks, or multiple times a week for a period of time, for example 3–5 times over a two week period. Generally, the amelioration of the autoimmune disease symptoms persists for some period of time, preferably at least months. Over time, the patient may experience a relapse of symptoms, at which point the treatments may be repeated.

In a preferred embodiment, the invention further provides kits for the practice of the methods of the invention, i.e., the incubation of the cells with the regulatory compositions. The kit may have a number of components. The kit comprises a cell treatment container that is adapted to receive cells from a patient with an antibody-mediated or cell-mediated autoimmune disorder. The container should be sterile. In some embodiments, the cell treatment container is used for collection of the cells, for example it is adaptable to be hooked up to a leukophoresis machine using an inlet port. In other embodiments, a separate cell collection container may be used.

In a preferred embodiment, the kit comprises a cell treatment container that is adapted to receive cells from a patient with a cell mediated disorder. The kit may also be adapted for use in a automated closed system to purify specific T cell subsets and expand them for transfer back to the patient.

The form and composition of the cell treatment container may vary, as will be appreciated by those in the art. Generally the container may be in a number of different forms, including a flexible bag, similar to an IV bag, or a rigid container similar to a cell culture vessel. It may be configured to allow stirring. Generally, the composition of the container will be any suitable, biologically inert material, such as glass or plastic, including polypropylene, polyethylene, etc. The cell treatment container may have one or more inlet or outlet ports, for the introduction or removal of cells, reagents, regulatory compositions, etc. For example, the container may comprise a sampling port for the removal of a fraction of the cells for analysis prior to reintroduction into the patient. Similarly, the container may comprise an exit port to allow introduction of the cells into the patient; for example, the container may comprise an adapter for attachment to an IV setup.

The kit further comprises at least one dose of an regulatory composition. "Dose" in this context means an amount of the regulatory composition such as cytokines, that is sufficient to cause an effect. In some cases, multiple doses may be included. In one embodiment, the dose may be added to the cell treatment container using a port; alternatively, in a preferred embodiment, the dose is already present in the cell treatment container. In a preferred embodiment, the dose is in a lyophilized form for stability, that can be reconstituted using the cell media, or other reagents.

In some embodiments, the kit may additionally comprise at least one reagent, including buffers, salts, media, proteins, drugs, etc. For example, mitogens, monoclonal antibodies and treated magnetic beads for cell separation can be included.

In some embodiments, the kit may additional comprise written instructions for using the kits.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference in their entirety.

EXAMPLES

Example 1

Treatment of PBMCs with a Mixture of IL-2 and TFG-β

Example 1 shows that the relatively brief treatment of PBMCs from SLE patients with IL-2 and TFG-β can result in the marked inhibition of spontaneous polyclonal IgG and autoantibody production. As discussed below, PBMC from 12 patients with active SLE were exposed to IL-2 with or without TGF-β for 3 days, washed and cultured seven more days. The mean decrease in IgG secretion was 79%. The strongest inhibitory effect was observed in cases with the most marked B cell hyperactivity. Spontaneous production of anti-nucleoprotein (NP) antibodies was observed in 4 cases and cytokine treatment of PBMC decreased autoantibody production by 50 to 96%. IL-2 inhibited antibody production by either TGF-β-dependent or independent mechanisms in individual patients. In a study of anti-CD2 stimulated IgG production in a patient with active SLE, we documented that IL-2 and TGF-β can reverse the enhancing effects of CD8+ T cells on IgG production and induce suppressive activity instead.

Methods

Study Subjects for Spontaneous Antibody Synthesis

Twelve subjects were chosen with a diagnosis of SLE that fulfilled ARA criteria for the classification of SLE (Arnett, F. C. et al. (1998), *Arthritis Rheum* 31: 315–324). These patients were all women, 8 Hispanic, 2 African American, and 2 Asian. The age of each patient and duration of disease is shown in Table 1. Five patients were hospitalized and 7 were outpatients. Those patients who were receiving corticosteroids or antimalarials are also indicated. 8 patients were untreated. Disease activity was assessed with SLAM (Liang, M. H. et al., (1989), *Arthritis Rheum* 32:1107–1118) and SLEDAI (Bombardier, C. et al. (1992), *Arthritis Rheum* 35:630–640) indices with mean values of 16.5 and 13.4 respectively.

(JES3-19F1) antibody, and control rat IgG2a, were kindly provided by Dr. Satwant Narula (Schering Plough Pharmaceuticals, Kenilworth, N.J.). Control murine IgG1 myeloma protein was purchased from Calbiochem, San Diego, Calif. Recombinant human IL-2 was purchased from Chiron, Emmeryville, Calif. Anti-CD2 secreting hybridomas antibodies used OKT11 were obtained from the American Type Culture Collection (ATCC), Rockville, Md. and GT2 was generously provided by A. Bernard, Nice, France). Other antibodies included: anti-CD4 (OKT4, ATCC), anti-CD8 (OKT8, ATCC; CD8, Dako, Carpenteria, Calif.), anti-CD11b (OKM1, ATCC), anti-CD16 (3G8), kindly provided by J. Unkeless, New York, N.Y.); anti-CD20 (Leu 16, Becton Dickinson, San Jose, Calif.) and anti-CD74 (L243, ATCC).

Isolation of Blood Mononuclear Cells

Peripheral blood mononuclear cells (PBMC) were prepared from heparinized venous blood by Ficoll-Hypaque (Pharmacia, Piscataway, N.J.) density gradient centrifugation. The mononuclear cells were washed in PBS with 5 mM EDTA (Life Technologies, Grand Island, N.Y.) to remove platelets, which are a rich source of TGF-β.

Cell Culture Procedures

Procedures for cell cultures have been described previously (Wahl, S. M. (1994), *J Exp Med* 180:1587–1590; Gray, J. D. et al. (1998), *J Immunol* 160:2248–2254). In brief, $2 \times 10^5$ of PBMC were cultured in serum-free AIM-V culture medium (Life Technologies) in the wells of 96-well flat bottom microtiter plate with or without the indicated cytokines. After three days of culture, the PBMC were washed three times then fresh serum-free medium was added. After a further 7 days at 37° C., supernatants were harvested and assayed for total IgG and autoantibodies reactive with calf thymus nucleoprotein (NP) by a solid phase enzyme-linked immunoadsorbant assay (ELISA), as described previously (Linker-Israeli, M. et al. (1990), *Arthritis Rheum* 33:1216–1225). The optical density (OD) readings were transformed into units/ml (U/ml) from a standard curve using positive and negative standards. Supernatants from PBMC culture of SLE patients (with high titers of anti-NP antibodies) and normal individuals were used as controls.

TABLE 1

Profile of SLE Patients

| Case | SEX | Age | Ethnicity | Duration | Medications | SLAM | SLEDAI | IgG (μ/ml) |
|---|---|---|---|---|---|---|---|---|
| 1 | F | 18 | AA | 3 yr | Nil | 13 | 9 | 13.7 |
| 2 | F | 37 | H | 6 mo | Nil | 23 | 13 | 13.0 |
| 3 | F | 29 | H | 1 yr | Nil | 15 | 6 | 2.6 |
| 4 | F | 32 | AA | 4 yr | Pred 5 mg Ohchlor 400 mg | 9 | 6 | 2.5 |
| 5 | F | 57 | A | 5 mo | Nil | 24 | 19 | 2.2 |
| 6 | F | 55 | H | 5 mo | Nil | 23 | 22 | 1.5 |
| 7 | F | 27 | H | 3 yr | Pred 20 mg Ohchlor 400 mg | 13 | 17 | 1.0 |
| 8 | F | 21 | H | 2 yr | Nil | 18 | 13 | 1.0 |
| 9 | F | 36 | H | 15 yr | Pred 20 mg Ohchlor 400 mg Aza 25 mg | 14 | 8 | 0.8 |
| 10 | F | 41 | A | 4 yr | Nil | 15 | 16 | 0.5 |
| 11 | F | 20 | H | 6 yr | Pred 25 mg | 11 | 16 | 0.4 |
| 12 | F | 25 | H | 1 yr | Nil | 21 | 16 | 0.4 |

Reagents

Recombinant TGF-β and monoclonal anti-TGF-β (1D11.16) antibody, a murine IgG1, were kindly provided by Dr. Bruce Pratt (Genzyme Pharmaceuticals, Farmington, Mass.). Recombinant IL-10 and monoclonal anti-IL-10

Statistical Analysis

The data were analyzed using Graph Pad, Prism software (San Diego, Calif.). We used analysis of variance (ANOVA) after log transformation of the data and the non-parametric Mann-Whitney test.

Anti-CD2 Induced IgG Synthesis

The effects of CD8+ T cells cultured with or without NK cells on anti-CD2 stimulated CD4+ T cells and B cells was examined in a patient with SLE in a normal control. CD4+ and CD8+ cells were prepared from nylon non-adherent lymphocytes by negative selection using immunomagnetic beads as described previously (Gray, J. D. et al. (1998), *J Immunol* 160:2248–2254). For CD4+ cells the nylon non-adherent cells were stained with antibodies to CD8, CD16, CD11b and CD74. The same antibodies were used to obtain CD8+ cells except that CD4 was substituted for CD8. Purity of CD4+ cells was 95% and CD8+ cells 89%. To obtain NK cells, PBMC were added to a nylon wool column and the eluted, non-adherent cells were immediately rosetted with AET treated sheep red blood cells. The non-rosetting fraction was then stained with anti-CD3 and anti-CD74 (anti-HLA-DR) antibodies and depleted of reacting cells using immunomagnetic beads (Dynal). This resultant population contained 98% CD56+ and <0.5% CD3+ and <0.5% CD20+ lymphocytes. Since SLE B cells spontaneously secrete large amounts of IgG and because of the large amount of blood needed to prepare sufficient numbers of B cells for these studies, we substituted resting B cells from a healthy donor for patient B cells in this study. To obtain B cells, nylon wool adherent cells were immediately rosetted with SRBC to remove any T cells, and treated with 5 mM L-leucine methyl ester for complete removal of monocytes and functional NK cells. The resulting population was >92% CD20+ and <0.5% CD3+.

Results

In 12 patients studied, spontaneous IgG ranged from 0.4 to 13.7 μg/ml (FIG. 1). Exposure of PBMC to IL-2±TGF-β for 72 hours decreased IgG synthesis in 8 of 12 cases studied by at least 50% (mean decrease 79%, p=0.008, Mann Whitney). The most dramatic decreases were observed in cases with the most marked B cell hyperactivity. The correlation between the amount of IgG secreted and percent inhibition by IL-2 and TGF-β was r=0.647, p=0.02.

We compared the effects of IL-2 and TGF-β alone to the combination of IL-2 and TGF-β. FIG. 2 shows that each of these cytokines also inhibited IL-2 production. However, after log transformation to achieve a normal distribution of the data and applying the Bonnferoni correction for multiple comparisons, analysis of variance revealed that only the combination of IL-2 and TGF-β resulted in significant inhibition (p=0.05).

IL-10 production is increased in SLE (Llorente, L. et al. (1993), *Eur Cytokine Network* 4:421–427) and this cytokine can inhibit production of both IL-2 and TGF-β. In 9 cases we also assessed the effect of anti-IL-10, but only a modest decrease of IgG synthesis was observed in some subjects and this difference was not statistically significant. Similarly, TNFα production is also decreased in a subset of patients with SLE (Jacob, C. O. et al. (1990), *Proc Natl Acad Sci* 87:1233–1237). Although this cytokine also increases the production of active TGF-β (Ohtsuka, K. et al., (198), *J Immunol* 160:2539–2545), the addition of TNFα to the cultures had minimal effects (results not shown).

We also examined SLE PBMC for spontaneous production of anti-nucleoprotein (NP) autoantibodies and found significant titers in 4 cases. In all cases exposure of PBMC to either IL-2 or IL-2 and TGF-β inhibited anti-NP production by at least 50 percent. TGF-β by itself was ineffective (Table 2). In these cases the effects of IL-2 by itself was equivalent to that the combination of IL-2 and TGF-β.

TABLE 2

Effect of treating PBMC with IL-2 and TGF-β on Spontaneous Autoantibody production in SLE

| Cytokine treatment | Anti-nucleoprotein antibody (U/ml) | | | |
|---|---|---|---|---|
|  | Case A: | Case B: | Case C | Case D |
| Nil | 308 (100)* | 312 (100) | 25 (100) | 73 (100) |
| TGF-β (10 pg/ml) | 282 (92) | 298 (96) | 26 (104) | ND |
| IL-2 & TGF-β | 29 (10) | 14 (4.5) | 12 (48) | 35 (48) |
| IL-2 | 23 (7.5) | 10 (3) | 11 (44) | ND |

*Percent of baseline values
PBMC from SLE patients were exposed to IL-2 (10 u/ml) and TGF-β (10 pg/ml) for 72 hours. The cells were washed and cultured for seven additional days. Anti-NP released into the supernatants was measured by an ELISA.

Previously we have reported that IL-2 increases the production of biologically active TGF-β (Ohtsuka, K. et al., (1998), *J Immunol* 160:2539–2545). It was, therefore, possible that al least some of the effects of IL-2 on spontaneous antibody synthesis were mediated by TGF-β. This possibility was investigated by determining whether the effects of IL-2 could be reversed by an anti-TGF-β neutralizing antibody. In the example shown in FIG. 3A, the addition of anti-TGF-β did not affect spontaneous IgG synthesis. Antagonism of TGF-β, however, did abolish the inhibitory effects of IL-2 on IgG synthesis. PBMC from this patient (Case C in Table 2) also spontaneously produced anti-NP antibody. Here also anti-TGF-β abolished the inhibitory effects of IL-2 on anti-NP production (FIG. 3B). In this subject, therefore, the inhibitory effects of IL-2 on spontaneous IgG and autoantibody synthesis were mediated by TGF-β. This effect of anti-TGF-β was documented in 4 of 8 cases studied. Thus, the inhibitory effects of IL-2 could either be TGF-β-dependent or independent. Examples of each effect are shown in Table 3.

TABLE 3

Effect of IL-2 and TGF-β on Spontaneous IgG Synthesis in SLE

| Cytokines Added | Patient A: TGF-β dependent inhibition G (μgm/ml) | Patient B: TGF-β independent inhibition IgG (μgm/ml) |
|---|---|---|
| Medium only | 2.5 (100)* | 2.6 (100) |
| TGF-β (10 pg/ml) | 1.4 (56) | 2.5 (96) |
| IL-2 & TGF-β | 0.4 (16) | 0.5 (19) |
| IL-2 & anti-TGF-β | 11.6 (464) | 0.5 (19) |
| IL-2 & IgG1 | 3.6 (144) | 0.6 (23) |

*Percent of baseline IgG synthesis

We had the opportunity to repeat the study of on SLE patient 28 days after initiation of steroid therapy (Table 4). Before treatment spontaneous IgG synthesis was greater than 2 µg/ml of IgG. Exposure of PBMC to IL-2 markedly inhibited IgG production and TGF-β had a moderate effect. Following corticosteroid therapy, spontaneous IgG production decreased by 75%. As before, exposure of PBMC to IL-2±TGF-β decreased IgG production by 50%. However, this inhibition was reversed by anti-TGF-β. Here again, this effect of IL-2 could be explained by upregulation of endogenous active TGF-β.

TABLE 4

Effect of Corticosteroid Therapy on Spontaneous IgG Synthesis in SLE

| Cytokines Added | Before Treatment Day 0 | After Treatment Day 28 |
|---|---|---|
| Nil | 2.2 | 0.6 |
| TGF-β (10 pg/ml) | 1.2 | 0.4 |
| IL-2 (10 U/ml) | 0.4 | 0.3 |
| IL-2 & TGF-β | 0.7 | 0.3 |
| IL-2 & anti-TGF-β | ND | 0.8 |
| IL-2 & IgG1 | ND | 0.6 |

*Percent of baseline IgG synthesis

In view of our previous studies in healthy subjects that IL-2 and TGF-β can induce activated CD+ T cells to down-regulate antibody production, we attempted to isolate and treat CD8+ T cells from SLE patients in this study. These experiments were unsuccessful because of the marked variability of spontaneous antibody synthesis and the large amount of blood required from patients with active SLE for cell separation procedures. However, we were able to obtain enough blood from one patient with active SLE to investigate the effect of IL-2 and TGF-β on CD8+ T cell modulation of anti-CD2 induced IgG synthesis. We have recently reported that unlike anti-CD3, a mitogenic combination of anti-CD2 monoclonal antibodies did not induce PBL to produce IgG (Gray, J. D. et al. (1998), *J Immunol* 160:2248–2254). An example is shown in FIG. 4A. This was because anti-CD2 stimulated NK cells to produce TGF-β, which in turn induced CD8+ T cells to down-regulate antibody production (Gray, J. D. et al. (1998), *J Immunol* 160:2248–2254). In this patient, as we have reported previously (Gray, J. D. et al. (1994), *J Exp Med* 180:1937–1942), CD8+ T cells enhanced IgG synthesis and this enhancement was markedly potentiated by the combination of NK cells and CD8+ T cells (FIG. 4B). By contrast IL-2 and TGF-β abolished the helper effects of SLE CD8+ T cells and enabled these cells to suppress IgG production. This inhibitory effect of IL-2 and TGF-β was dependent upon the presence of CD8+ T cells. (FIG. 4C). Thus, evidence has been obtained that the effects of IL-2 and TGF-β can be mediated by CD8+ T cells.

These studies demonstrate that a short exposure of PBMC to IL-2 and TGF-β can greatly decrease subsequent spontaneous polyclonal IgG and autoantibody production in SLE, especially in patients with severe disease and marked B cell hyperactivity. This study confirms previous reports indicating that IL-2 can inhibit antibody production (Hirohata, S. et al. (1989), *J Immunol* 142: 3104–3112 and Fast, L. D. (1992), *J Immunol* 149:1510–1515) and reveals that picomolar concentrations of TGF-β can contribute to this down-regulation. In the group of 12 patients studied, the inhibitory effect of IL-2 and TGF-β on polyclonal IgG synthesis was greater than the effect of IL-2 alone. However, the inhibitory effects of IL-2 were heterogeneous. In 4 of 8 cases studied, the inhibition was TGF-β-dependent in that a neutralizing anti-TGF-β mAb abolished the effect. In the remaining cases the down-regulatory effects of IL-2 were TGF-β-independent. Similarly, both TGF-β-dependent and independent inhibition of spontaneous anti-NP autoantibody production was documented. We also investigated the effects of antagonizing the IL-10 and adding TNF-α because of previously described abnormalities in the production of these cytokines in SLE (Llorente L. et al. (1993), *Eur Cytokine Network* 4:421–427; Jacob, C. O. et al. (1990), *Proc Natl Acad Sci* 87:1233–1237). These procedures, however, had minimal effects on spontaneous antibody synthesis where lymphocytes had been activated previously.

Others have reported that the degree of B cell hyperactivity in SLE correlates with disease activity (Blaese, R. M. et al. (1980), *Am J Med* 69:345–350; Klinman, D. M. et al. (1991), *Arthritis Rheum* 34:1404–1410). This was not the case in the present study, possibly because of concurrent drug therapy. In general, those patients with marked spontaneous antibody synthesis were untreated whereas those with less B cell activity were currently receiving prednisone. We presented one case where spontaneous IgG synthesis decreased markedly after corticosteroid therapy was begun. This patient's B cells had also been secreting anti-NP antibody before treatment, and production of this autoantibody became undetectable after steroid therapy (result not shown).

TGF-βs consist of a multifunctional family of cytokines important in tissue repair, inflammation and immunoregulation (Massague, J. (1990), *Annu Rev Cell Biol* 6597–641). TGF-β is different from most other cytokines in that it is secreted as an inert precursor molecule and converted to its biologically active form extracellularly (Massague, J. (1990), *Annu Rev Cell Biol* 6597–641; Flaumenhaft, R. et al. (1993), *Adv Pharmacol* 24:51–76). Regulatory T cells in various experimental autoimmune models such as experimental autoimmune encephalitis (Weiner, H. L. et al. (1994), *Annu Rev Immunol* 12:809–837) and colitis (Neurath, M. F. et al. (1996), *J Exp Med* 183:2605–2516) produce this cytokine. TGF-β is immunosuppressive in nanomolar concentrations and can inhibit T and B cell proliferation, NK cell cytotoxic activity and the generation of T cell cytotoxicity (Letterio, J. J. et al. (1998), *Ann Rev Immunol* 16:137–162). By contrast, TGF-β has been reported to promote the growth of murine CD4+ cells and CD8+ cells (Kehrl, J. H. et al. (1986), *J Exp Med* 163:1037–1050; Lee, H. M. et al. (1993), *J Immunol* 151:668–677) and can promote B cell differentiation (Van Vlasselaer, P. et al. (1992), *J Immunol* 148:2062–2067).

In our previous studies with lymphocytes from healthy subjects to generate regulatory T cells, the picomolar concentrations of TGF-β used were smaller than that required for inhibition of T or B cell function (Gray, J. D. et al. (1998), *J Immunol* 160:2248–2254; Gray, J. D. et al. (1994), *J Exp Med* 180:1937–1942). Similar concentrations were used in the present studies with SLE patients and TGF-β by itself had modest inhibitory effects on antibody synthesis. As before, a combination of IL-2 of TGF-β produced the most potent inhibition. In our previous studies, this effect was mediated by CD8+ T cells.

IL-2 has well established effects on the induction of T suppressor cell activity (Hirohata, S. et al. (1989), *J Immunol* 142:3104–3112; Fast, L. D. *J Immunol* 149:1510–1515), but whether these effects are direct or indirect is unclear. In mice deletion of the IL-2 gene results in massive lymphoproliferation and autoimmune disease (Sadlack, B. et al. (1995), *Eur J Immunol* 25:3053–3059). In SLE, a negative correlation was reported between IL-2 levels and B cell hyperactivity (Huang, Y. P. et al. (1988), *J Immunol* 141:827–833). Previously, we attempted to inhibit spontaneous antibody production in SLE with IL-2, but the results, however were extremely variable. While we observed strong inhibition in some cases, in others IL-2 markedly increased antibody production. We believe that the timing and the cytokine milieu explains the more consistent inhibition observed in this study. Here the IL-2 and TGF-β were present only during the initial 72 hours of culture rather than the entire culture period. Enhancement of antibody synthesis in the latter case could be explained by the positive effects of IL-2 on B cell differentiation (Coffman, R. L. et al. (1988), *Immunol Rev* 102:5–28). IL-2 can down-regulate antibody production by several mechanisms. In addition to the TGF-β circuit described in the report, IL-2 induced inhibition can occur by up-regulation of IFN-γ (Noble, A. et al. (1998), *J Immunol* 160:566–571), or by cytolytic mechanisms (Stohl, W. et al. (1998), *J Immunol* 160:5231–5238; Esser, M. T. et al. (1997), *J Immunol* 158:5612–5618).

Previously, we had investigated the regulatory effects of NK cells on antibody synthesis and reported that while the direct effect of NK cells is to up-regulate IgG synthesis (Kinter, A. et al. (1995), *Proc Natl Acad Sci USA* 92:10985–10989), these lymphocytes have the opposite effect when cultured with CD8+ T cells in healthy subjects (Gray, J. D. et al. (1994), *J Exp Med* 180:1937–1942). In SLE patients, however, the combination of CD8+ T cells and NK cells enhanced IgG production (Linker-Israeli, M. et al. (1990), *Arthritis Rheum* 33:1216–1225). This was again observed in the present report. While in the normal subject the addition of NK cells to CD8+ T cells markedly inhibited anti-CD2 stimulated IgG synthesis, the opposite was observed in SLE. From studies of normals we had learned that NK cell-derived TGF-β induced co-stimulated CD8+ T cells to down-regulate IgG and IgM production (Gray, J. D. et al. (1998), *J Immunol* 160:2248–2254). In this study IL-2 and TGF-β induced moderate suppressive activity by CD8+ T cells. It is likely, therefore, that in SLE at least one way that IL-2 and TGF-β inhibit B cell activity is by generating regulatory T cells. In addition, other lymphocyte populations treated with these or other cytokines may also down-regulate B cells activity in SLE.

Example 2

The Correlation of TGF-β Production to Disease Activity and Severity

Having shown that the lymphocyte production of the total and active forms of TGF-β is decreased, we next asked whether these defects correlate with disease activity and/or severity. TGF-β1 production by blood lymphocytes from 17 prospectively studied SLE patients was compared with 10 rheumatoid arthritis (RA) patients and 23 matched healthy controls. In RA the levels of active TGF-β1 were lower than controls, but not deceased to the extent found in SLE. Levels of constitutive and anti-CD2 stimulated active TGF-β1 detected in picomolar amounts were markedly reduced in 6 untreated patients hospitalized with recent onset, very active and severe SLE and similarly reduced in 11 patients with treated, less active disease, thus, decreased production of active TGF-β1 did not correlate with disease activity. By contrast, decreased production of total TGF-β1 inversely correlated with disease activity. Thus it appears that although impaired lymphocyte secretion of the latent precursor of TGF-β1 may result as a consequence of disease activity, the ability to convert the precursor molecule to its active form may be an intrinsic cellular defect. Insufficient exposure of T cells to picomolar concentrations amounts of TGF-β1 at the time they are activated can result in impaired down-regulation of antibody synthesis. Thus, decreased lymphocyte production of active TGF-β1 in SLE can contribute to B cell hyperactivity characteristic of this disease.

Methods

Study Subjects

Seventeen subjects with a diagnosis of SLE who fulfilled the American College of Rheumatology criteria for the classification of SLE (Tan, E. M. et al. (1982), *Arthritis Rheum* 25:1271–1277), 10 subjects with RA who fulfilled the ACR 1987 revised criteria for the classification of RA (Arnett, F. C. et al. (1988), *Arthritis Rheum* 31:315–324), and 23 healthy donors were studied. The SLE group consisted of 15 women and 2 men (15 Hispanic, 1 African American, 1 Asian). The mean age was 34.5 years (range, 20–75 years). Six patients were hospitalized, and 11 were attending an outpatient clinic. All of the hospitalized patients were untreated before admission and were studied before they received their first dose of corticosteroids. Outpatients were receiving less than 20 mg of prednisone, and none were receiving cytotoxic drugs. Disease activity was assessed with the SLAM (Liang, M. H. et al. (1989), *Arthritis Rheum* 32:1107–1118) and SLEDAI (Bombardier, C. et al. 1992), *Arthritis Rheum* 35:630–640) indices with mean values of 6.6 and 7.6, respectively. The RA group consisted of 9 women and 1 man (9 Hispanic, 1 Asian). The mean age was 50.9 years (range, 39–67 years). All of the patients were attending the outpatient clinic and had mild to moderately active disease. The mean duration of disease was 9.5 years. One patient received myochrysine, 3 patients received prednisone (1, 1 and 20 mg), 3 patients received methotrexate, and one patient received sulphasalazine. Healthy donors served as controls and were matched as closely as possible for age, sex, and ethnic groups.

TABLE 5

Clinical Characteristics of Two Groups of SLE Patients

| Clinical Data | Hospitalized (n = 6) | Outpatient (n = 11) | p Value |
| --- | --- | --- | --- |
| Age | 26.8 | 38.6 | 1.037 |
| Sex (F/M) | 6/0 | 9/2 | |
| Ethnic Group (H/AA/A) | 5/0/1 | 10/1/0 | |
| Disease Duration (yr) | 0.71 | 8.25 | 0.051 |
| Disease Activity | | | |
| SLAM | 13.3 | 2.9 | 0.014 |
| SLEDAI | 15.7 | 4.1 | 0.006 |
| Prednisone dose (mg/day) | 41.2 | 7.8 | 0.008 |
| Active Renal disease | 83% | 9% | 0.028 |
| Hemolytic Anemia | 67% | 9% | 0.064 |
| Anti-DNA (titer) | 466.7 | 33.0 | 0.064 |
| C3 | 47.5 | 98.6 | 0.008 |
| C4 | 13.7 | 18.6 | 0.127 |

Reagents

Antibodies used were supernatants of hybridomas secreting anti-CD2 (OKT11, American Type Culture Collection (ATCC), Rockville, Md., and GT2 made available by Dr. Alain Bernard, Nice, France). A monoclonal antibody recognizing TGF-β isoforms 1,2 &3 (1D11), an antibody against TGF-β isoforms 2&3 (3C7), and rTGF-β2 were kindly provided by Dr. Bruce Pratt (Genzyme Pharmaceuticals, Farmington, Mass.).

Isolation of Blood Lymphocytes

Peripheral blood mononuclear cells (PBMC) were prepared from heparinized venous blood by Ficoll-Hypaque (Pharmacia, Piscataway, N.J.) density gradient centrifugation using methods described previously (Ohtsuka, K. et al. (1998), *J Immunol* 160:2539–2545). The mononuclear cells were washed in PBS with 5 mM EDTA (Life Technologies, Grand Island, N.Y.) to remove platelets, which are a rich source of TGF-β. Peripheral blood lymphocytes (PBL) were separated from PBMC by centrifugation through a continuous Percoll (Pharmacia) density gradient. The percentage of monocytes remaining in the high density, lymphocyte-enriched fraction was somewhat higher in SLE (8.5% vs 4.3%).

Cell Culture Procedures

Procedures for cell cultures have been described previously ((Ohtsuka, K. et al. (1998), *J Immunol* 160:2539–2545). In brief, $1 \times 10^5$ of the lymphocytes were added to the wells of 96-well flat bottom microtiter plate (Greiner Rocky Mountain Scientific, Salt Lake City Utah). The cultures were carried out in AIM-V serum free medium (Life Technologies), since serum contains significant amount of latent TGF-β. Anti-CD2 was used at the optimal concentrations to induce TGF-β production (GT2 1:40 and T11 1:80) hybridoma culture supernatants. Previous studies have revealed that anti-CD2 strongly stimulates PBL to produce TGF-β (Gray, J. D. et al. (1998), *J Immunol* 160:2248–2254).

TGF-β Assay

Mink lung epithelial cells (MLEC) which had been transfected with an expression construct containing a plasminogen activator inhibitor (PAI-1) promoter fused to luciferase reporter gene were kindly provided by Dr D. B. Rifkin, New York, N.Y. MLEC at $2 \times 10^4$/well were incubated with 200 μl supernatants for 18 h at 37° C. To assay for luciferase activity, MLEC were lysed by a cell lysis reagent (Analytical Luminescence, Ann Arbor, Mich.). Cell lysates were then reacted with assay buffer and luciferin solution (both from Analytical Luminescence) immediately before being measured in a luminometer (Lumat, Berthold Analytical Instruments Inc., Nashua, N.H.). To measure total TGF-β activity, samples were heated at 80° C. for 3 minutes to release the active cytokine from the latent complex. Active TGF-β activity was measured without heating of supernatants. In all assays, several concentrations of rTGF-β were included to generate a standard curve. The variability of replicate cultures was less than 10 per cent (Ohtsuka, K. et al. (1998), *J Immunol* 160:2539–2545).

Statistical Analysis

The significance of the results was analyzed using the Mann-Whitney test and Spearman rank correlation performed using GBSTAT software (Professional Statistics and Graphics Computer Program, Dynamic Microsystems Inc., Silver Spring, Md.).

Results

We measured constitutive and stimulated TGF-β1 produced by PBL from patients with SLE or RA, and compared these values with those from normal controls. The cytokine detected in culture supernatants was neutralized by a mAb recognizing isoforms 1,2,&3, but not by one against isoforms 2&3, a result confirming the production of TGF-β1. Compared to normal controls, constitutive production of active TGF-β1 was significantly decreased in SLE (14±5 vs 56±21 pg/ml, p=0.02, FIG. 5). Anti-CD2 stimulated active TGF-β1 was also decreased (87±22 vs 399±103 pg/ml, p=0.003). In RA, the mean value for constitutive TGF-β1 was similar to that of SLE (19±5 pg/ml) and after stimulation by anti-CD2 was intermediate between normal and SLE (197±54 pg/ml; FIG. 5).

Constitutive total TGF-β1 produced by lymphocytes was also decreased in SLE in comparison with the normal group (286±82 vs 631±185 pg/ml, p=0.05). The value in RA was intermediate between normal and SLE (435±161 pg/ml). Following the addition of anti-CD2, total TGF-β1 increased in SLE somewhat more than in normal controls so that the differences were not statistically significant. Values in the RA group were again intermediate between the normal and SLE group.

To look for a possible relationship between decreased levels of TGF-β1 and disease activity, we compared hospitalized SLE patients with those seen in the outpatient clinic. The clinical characteristics of these two groups are summarized in Table 5. Those that were hospitalized were younger; 5 of 6 had symptoms for less than 3 months; they had markedly active disease; and most had severe SLE with nephritis and/or hemolytic anemia. The outpatient group by contrast, had chronic disease which had become less active following treatment. Notwithstanding this marked difference in disease heterogeneity, duration, activity, and severity, both constitutive and stimulated active TGF-β1 production were significantly decreased in both groups in comparison with normal controls (Table 6).

TABLE 6

Comparison of TGF-β1 Production by Lymphocytes from Two Groups of Patients with SLE*

| | | SLE | |
| --- | --- | --- | --- |
| | Normal (n = 23) | Group 1 (n = 6) | Group 2 (n = 11) |
| Active TGF-β1 (pg/ml) | | | |
| Constitutive | 56 ± 21 | 21 ± 14† | 10 ± 4† |
| CD2 stimulated | 399 ± 103 | 117 ± 52† | 70 ± 19‡ |
| Total TGF-β1 (pg/ml) | | | |
| Constitutive | 631 ± 185 | 132 ± 44† | 365 ± 120 |
| CD2 stimulated | 771 ± 136 | 226 ± 74† | 667 ± 166 |

*PBL $1 \times 10^5$/well were cultured for 48 h, and the supernatants were tested for TGF-β1.
SLE patients were divided into 2 groups. Group 1: Hospitalized patients. Group 2: Outpatient clinic patients.
p values indicate comparison between the SLE group indicated and the normal controls as assessed by the Mann-Whitney test; † $p < 0.05$, ‡ $p < 0.01$.

When we looked for correlations between levels of active and total TGF-β1 with disease activity, there was a significant negative correlation between anti-CD2 stimulated production of total TGF-β1 and the SLEDAI (r=−0.55, p=0.03, but not the SLAM index (−0.43, p=11). The SLEDAI index is weighted for central nervous system involvement and renal disease. Thus, an impaired capacity for lymphocytes to secrete the precursor form of TGF-β1 appears to be associated with severe disease. The Levels of active TGF-β1 did not correlate with disease activity.

The principal finding in this example is that decreased production of active TGF-β1 in SLE does not correlate with disease activity or severity. Decreased amounts of constitutive and stimulated active TGF-β1 were found in both patients with recent onset and established disease. Moreover, the values did not correlate with activity, as measured by the SLAM and SLEDAI indices, or severity as assessed by vital organ involvement. However, while total TGF-β1 production was also decreased in SLE, this defect appeared to correlate with disease activity. It was found chiefly in hospitalized SLE patients. The finding that total TGF-β1 production correlated most strongly with the SLEDAI index, which is weighted for major organ system involvement, also suggests a relationship with disease severity.

This study also included a control group of RA patients whose disease activity was comparable to SLE patients with established disease. Although TGF-β1 values in the RA group was somewhat less than the normal controls, with the exception of constitutive active TGF-β1, the magnitude of the defect was not as marked as in SLE and was not statistically significant.

Previously, we have documented that NK cells are the principal lymphocyte source of TGF-β and the only lymphocyte population to constitutively produce this cytokine in its active form (Gray, J. D. et al. (1998), *J Immunol* 160:2248–2254). It was of interest, therefore, to find that constitutive production of NK cell-derived TGF-β was decreased in SLE. We also learned that both IL-2 and TNF-α could enhance the production of active TGF-β. Production of both of these cytokines are decreased in SLE (Gray, J. D. et al. (1994), *J Exp Med* 180:1937–1942). However, in most patients exogenous IL-2 and TNF-α could not restore TGF-β production to normal (Example 2). IL-10 production is increased in SLE (Llorente, L. et al. (1993), *Eur Cytokine Network* 4:421) and correlations between elevated levels and disease activity have been reported (Houssiau, F. A. et al. (1995), *Lupus* 4:393–395; Haglwara, E. et al. (1996), *Arthritis Rheum* 39:379). IL-10 can inhibit IL-2, TNF-α and TGF-β production (Example 2 and Moore, K. W. et al. (1993), *Ann Rev Immunol* 11:165–190). The findings that production of active TGF-β is decreased in patients with mild as well as active disease, and that we could only partially reverse the production defect by antagonizing IL-10 (Example 2), suggests that increased IL-10 production, by itself, cannot account for decreased lymphocyte production of active TGF-β1 in SLE. Several mechanisms are probably involved. It is likely that one or more defects in the extracellular conversion of the latent precursor to the mature, active form may explain this abnormality.

Although TGF-β has well documented inhibitory properties on lymphocyte proliferation and effector cell function (Letterio, J. J. et al. (1998), *Ann Rev Immunol* 16:137–162), stimulatory properties have also been reported (Lee, H. M. et al. (1991), *J Immunol* 151:668–677). TGF-β modulates cytokine production by stimulated T cells as well as up-regulating its production. In mice, TGF-β1 selectively activates CD8+ T cells to proliferate (Lee, H. M. et al. (1991), *J Immunol* 151:668–677), and augments the maturation of naive cells to memory T cells (Lee, H. M. et al. (1991), *J Immunol* 147:1127–1133). In humans TGF-β1 is a potent inducer of effector T cells (Cerwenka, A. et al. (1994), *J Immunol* 153:4367–4377). While large (nanogram/ml) quantities are required for immuno-suppressive effects, we have shown that only small (picogram/ml) quantities are needed to co-stimulate CD8+ T cells for down-regulatory effects on antibody production (Gray, J. D. et al. (1998), *J Immunol* 160:2248–2254).

These studies suggest, therefore, that while impaired lymphocyte secretion of the latent precursor of TGF-β1 may result as a consequence of disease activity, decreased active TGF-β1 production in SLE is more complex and may result from several different mechanisms. We have proposed that programming naive T cells to down-regulate antibody production requires the presence of pg/ml quantities of active TGF-β at the time they are activated and have evidence to support this suggestion (Gray, J. D. et al. (1998), *J Immunol* 160:2248–2254). Therefore, a lack of picomolar amounts of active TGF-β in the local environment at a critical time could possibly account for ineffective T cell regulatory function to control B lymphocyte activity in SLE.

Example 3

Treating SLE with Mitogens

In this example, IgG production is down regulated by treating the cells with an regulatory composition comprising a mitogen such as a combination of mitogenic anti-CD2 monoclonal antibodies. These antibodies may be added in soluble form or immobilized on beads to cross link receptors on T cells and NK cells. The cells are prepared as outlined in the above examples, and then they are incubated with mitogens to augment the population of cells that down regulate antibody production. Con A is available from Sigma (St. Louis, Mo.).

Although it is not known how anti-CD2 works, it is believed that these antibodies induce NK cells in the PBMC preparation to secrete active TGF-β (Ohtsuka, K. et al. (198), J Immunol 160:2539–2545); TGF-β then acts on T cells to become antibody suppressor cells.

The cells are then washed, if necessary, and transplanted back into the patient.

Example 4

Treating Cells with a Mixture of Cytokines and Mitogens

Cells are prepared as outlined above, and incubated with an regulatory composition comprising a mixture of mitogen and cytokine to induce populations of cells that down regulate antibody production. An example of this approach is shown in FIG. 4C. In this example, maximum induction of suppression was obtained by treating CD4+ cells and CD8+ cells with Con A, IL-2 and TGF-β for.

For the preparation of regulatory T cells that will be transferred back to the patient anti-CD2 and/or anti-CD3 monoclonal antibodies will be used instead of Con A to activate T cells. The regulatory composition contains TGF-β with or without IL-2. The cells are incubated with the composition for 4 to 72 hours using standard incubation techniques in a closed system such as the Nexell 300i.Magnetic Cell Selection System.

Following incubation, the cells are washed with HBBS to remove any cytokine and mitogen in the solution. The cells are optionally further expanded by culturing with anti-CD3±anti-CD28 immobilized on beads. The cells are suspended in 200–500 ml of HBBS and reintroduced into a patient.

Example 5

Treating Cells to Normalize Cell-mediated Immunity

Contributing to autoantibody production in SLE is an imbalance between IL-10 and TNF-α production. Levels of IL-10 are excessive and levels of TNF-α are decreased (Llorente et al. 1995. J Exp. Med. 181:839–44) (Houssiau, F. A. et al., 1995. Lupus 4:393–5. (Ishida, H. et al. 1994. J Exp. Med. 179:305–10) (Jacob, C. O. and McDevitt, H. O., 1988. Nature 331:356–358). We have evidence that this imbalance is corrected by strongly activating T cells in the presence of TGF-β and have recently elucidated the mechanism of action of this effect.

Purified T cells were prepared as outlined above, and incubated with ConA and IL-2 with or without TGF-β. FIG. 6 shows that T cell stimulation in the absence of TGF-β, resulted in increased production of IL-10. However, when TGF-β was added to stimulated T cells, IL-10 production was blocked and production of TNF-α was increased. In addition, TNFR2 expression was increased significantly. Without being bound by theory, It is believed that accelerated TNF-α signaling via TNFR2 induced by TGF-β results in regulatory T cells that inhibit antibody production. Our results support this suggestion.

We have determined that upregulation of TNF-α by TGF-β is essential for the induction of regulatory T cells. FIG. 7 shows two experiments where the addition of TGF-β to activated CD8+ T cells resulted in marked suppression of IgG production. This suppressive activity depended upon TNF-α as an essential intermediate. In each of these experiments, a neutralizing anti-TNF-α antibody completely abolished the suppressive effects of the CD8+ regulatory T cells (CD8reg).

Patients with SLE have a marked defect in cell-mediated immunity with impaired production of IL-2, TNF-α and IFN-γ. (Horwitz, D. A. et al. (1997), *Dubois' Lupus Erythematosus,* 5th Ed. (1997), pp. 83–96, D. J. Wallace et al. eds., Williams and Wilkins, Baltimore). Without being bound by theory, it is believed that the defect in lymphocyte production of TGF-β is partially responsible for impaired production of IL-2, TNF-α and IFN-γ. We have found that stimulation of T cells in the presence of TGF-β significantly increased production of IL-2, TNF-α and IFN-γ when these cells were restimulated. Moreover, this result was dependent upon upregulation of TNF-α by TGF-β (see FIG. 8).

We have evidence that TGF-β production is decreased in SLE and that this defect contributes to the imbalance between IL-10 and TNF-α. Without being bound by theory, it is believed that high levels of IL-10 in SLE sustain autoantibody production and are responsible for decreased production of TNF-α, IL-2, IFN-γ. Decreased production of these cytokines is responsible for defective cellular immunity in SLE. We have demonstrated that under specified conditions, TGF-β down-regulates IL-10 and enhances the production of TNF-α. Down-regulation of IL-10 and enhancement of TNF-α production by TGF-β plays a crucial role in the normalization of regulatory T cell activity in SLE, restoration of cell-mediated immunity and remission of disease.

Example 6

Generation of Regulatory T Cells that Suppress Cell-mediated Autoimmunity

The previous examples used regulatory compositions to treat antibody-mediated autoimmune diseases. Similar compositions are used to induce CD4+ as well as CD8+ T cells to suppress cell-mediated autoimmune diseases. We show that CD8+ or CD4+ cells conditioned by TGF-β alone suppressed the generation of T cell cytotoxicity.

Instead of using mitogens to induce regulatory T cells, the allogeneic mixed lymphocyte reaction is used for this purpose. In this reaction, T cells from one individual recognize and respond to foreign histocompatibility antigens displayed by other individuals PBMCs. These responder T cells proliferate and develop the capacity to kill these target cells.

To develop suppressor T cells, various CD4+ and CD8+ T cell subsets from one individual (donor A) were cultured with irradiated T cell-depleted mononuclear cells from another individual (donor B). The cells were cultured for 5 days with or without TGF-β (1 ng/ml) in the suspensions. After this time, TGF-β was removed and the cells added to fresh T cells from donor A and non-T cells from donor B. FIG. 9 shows TGF-β induced both CD4+ and CD8+ T cell subsets to develop the capacity to inhibit cell mediated cytotoxicity. FIG. 10 shows two additional experiments with CD4+ regulatory T cells induced by TGF-β.

Further studies revealed that regulatory CD4+ T cells generated in this manner have a unique mode of action. Unlike the CD8+ and CD4+ T cells generated previously which suppress by secreting inhibitory cytokines, these allo-specific regulatory CD4+ T cells have a contact dependent mechanism of action (FIG. 11). Without being bound by theory, it is believed that these regulatory T cells suppress other T cells from being activated. Addition of these T cells to responder T cells and allo-stimulator cells inhibited proliferation (FIG. 12) and decreased the ability of responder CD8+ killer precursor cells to become activated (FIG. 13).

We also learned that these regulatory CD4+ cells express IL-2 receptors (CD25) on their cell surface and were extremely potent (FIG. 14). Decreasing the proportion of regulatory CD4+ cells to responder T cells from 1:4 (20%) to 1:32 (3%) only minimally decreased the inhibitory effects of these cells.

Because only a few of these cells are needed for potent down-regulatory effects, it is likely that a sufficient number can be transferred to patients to suppress autoimmunity or other desired immunosuppressive effects, such as inhibiting of graft rejection.

Example 7

Stimulating CD4+ T Cells to Produce Immunosuppressive Levels of TGF-β

CD4+ T cells that produce immunosuppressive levels of TGF-β have been named Th3 cells, but the mechanisms involved in their development are poorly understood. We have obtained evidence that strong stimulation of CD4+ cells with the superantigen, staphylococcus enterotoxin B (SEB), or repeated stimulation of CD4+ cells stimulated with a lower concentration of SEB induced these cells to produce immunosuppressive levels of active TGF-β.

FIG. 15 shows increased production of both active and total TGF-β produced by CD4+ T cells stimulated with increasing concentrations of SEB. FIG. 16 shows the effect of repeated stimulation of CD4+ T cells with low doses of SEB. By the third time these T cells were stimulated with SEB, they produced significant amounts of the active form of TGF-β.

FIG. 17 shows the effects of SEB on naive (CD45RA+ CD45RO−) CD4+ and CD8+ T cells. The cells were stimulated with SEB every 5th day for a total of three stimulations. The percentages of each T cell subset and the cells expressing the CD25 IL-2 receptor activation marker were determined after each stimulation. Panels A and C show that by including TGF-β 1 ng/ml in the initial stimulation, CD4+ T cells became the predominant subset in the cultures after repeated stimulation. Panels B and D show that CD25 expression by SEB stimulated cells decreased by the third stimulation in control cultures. However, CD25 expression remained very high if the T cells were primed with TGF-β. Thus, TGF-β appears to have preferential effects on CD4+ cells if these T cells are repeatedly stimulated and almost all of these cells were CD25+ after culture for 20 days.

In summary, following T cell stimulation, the predominant regulatory effects of TGF-β are directed to CD8+ cells. Upon repeated stimulation, this cytokine now induces CD4+ cells to become regulatory cells and these cells are more potent than CD8+ cells in their suppressive activities.

What is claimed is:

1. A method for treating an autoimmune disorder in a patient comprising:
   a) removing peripheral blood mononuclear cells (PBMC) from said patient;
   b) treating said cells with a regulatory composition to generate regulatory T cells; and c) reintroducing said regulatory T cells to said patient to suppress an aberrant immune response.

2. A method according to claim 1 wherein said aberrant immune response is a cell-mediated autoimmune disease selected from the group consisting of Hashimoto's disease, polymyositis, disease inflammatory bowel disease, multiple sclerosis, diabetes mellitus, rheumatoid arthritis, and scleroderma.

3. A method for treating an autoimmune disorder in a patient comprising:
   a) removing peripheral blood mononuclear cells (PBMC) from said patient;
   b) treating said cells with a regulatory composition to induce said cells to produce immunosuppressive levels of TGF-β; and
   c) reintroducing said cells to said patient to suppress aberrant immune responses.

4. A method according to claim 1 or 3 wherein said PBMCs comprise CD4+ T cells and said regulatory composition comprises TGF-β.

5. A method according to claim 1 or 3 wherein said PBMCs comprise CD8+ T cells and said regulatory composition comprises TGF-β.

6. A method according to claim 1 or 3 wherein said PBMCs comprise CD4+ T cells and CD8+ T cells and said regulatory composition comprises TGF-β.

7. A method according to claim 1 or 3 wherein said PBMCs comprise CD4+ T cells and said regulatory composition comprises TGF-β and IL-2.

8. A method according to claim 1 or 3 wherein said PBMCs comprise CD8+ T cells and said regulatory composition comprises TGF-β and IL-2.

9. A method according to claim 1 or 3 wherein said PBMCs comprise CD4+ T cells and CD8+ T cells and said regulatory composition comprises TGF-β and Il-2.

10. A method according to claim 1 or 3 wherein said PBMCs comprise CD4+ T cells and said regulatory composition comprises a mixture of TGF-β and anti-CD2.

11. A method according to claim 1 or 3 wherein said PBMCs comprise CD8+ T cells and said regulatory composition comprises a mixture of TGF-β and anti-CD2.

12. A method according to claim 1 or 3 wherein said PBMCs comprise CD4+ T cells and CD8+ T cells and said regulatory composition comprises a mixture of TGF-β and anti-CD2.

13. A method according to claim 1 or 3 wherein said PBMCs comprise CD4+ T cells and said regulatory composition comprises a mixture of TGF-β, IL-2 and anti-CD2.

14. A method according to claim 1 or 3 wherein said PBMCs comprise CD8+ T cells and said regulatory composition comprises a mixture of TGF-β, IL-2 and anti-CD2.

15. A method according to claim 1 or 3 wherein said PBMCs comprise CD4+ T cells and CD8+ T cells and said regulatory composition comprises a mixture of TGF-β, IL-2 and anti-CD2.

16. A method according to claim 1 or 3 wherein said PBMCs comprise CD4+ T cells and said regulatory composition comprises a mixture of TGF-β and anti-CD3.

17. A method according to claim 1 or 3 wherein said PBMCs comprise CD8+ T cells and said regulatory composition comprises a mixture of TGF-β and anti-CD3.

18. A method according to claim 1 or 3 wherein said PBMCs comprise CD4+ T cells and CD8+ T cells and said regulatory composition comprises a mixture of TGF-β and anti-CD3.

19. A method according to claim 1 or 3 wherein said PBMCs comprise CD4+ T cells and said regulatory composition comprises a mixture of TGF-β, IL-2 and anti-CD3.

20. A method according to claim 1 or 3 wherein said PBMCs comprise CD8+ T cells and said regulatory composition comprises a mixture of TGF-β, IL-2 and anti-CD3.

21. A method according to claim 1 or 3 wherein said PBMCs comprise CD4+ T cells and CD8+ T cells and said regulatory composition comprises a mixture of TGF-β, IL-2 and anti-CD3.

22. A method according to claim 1 or 3 wherein said PBMCs comprise NK T-cells and said regulatory composition comprises TGF-β.

23. A method according to claim 1 or 3 wherein said PBMCs comprise NK T-cells and said regulatory composition comprises TGF-β and IL-2.

24. A method according to claim 1 or 3 wherein said PBMCs comprise NK T-cells and said regulatory composition comprises TGF-β, IL-2 and anti-CD2.

25. A method according to claim 1 or 3 wherein said PBMCs comprise NK T-cells and said regulatory composition comprises TGF-β, IL-2 and anti-CD3.

26. A method according to claim 3 wherein said wherein said aberrant immune response is an antibody mediated disease selected from the group consisting of pemphigus vulgaris, myasthenia gravis, hemolytic anemia, thrombocytopenia purpura, Grave's disease, dermatomyositis and Sjogren's disease.

* * * * *

UNITED STATES PATENT AND TRADEMARK OFFICE
CERTIFICATE OF CORRECTION

| | | |
|---|---|---|
| PATENT NO. | : 6,797,267 B2 | Page 1 of 1 |
| APPLICATION NO. | : 10/028944 | |
| DATED | : September 28, 2004 | |
| INVENTOR(S) | : Horwitz | |

It is certified that error appears in the above-identified patent and that said Letters Patent is hereby corrected as shown below:

IN THE SPECIFICATION

Col. 1, Line 13, please insert heading immediately preceding the heading FIELD OF THE INVENTION: --STATEMENT AS TO FEDERALLY SPONSORED RESEARCH--

Under the heading STATEMENT AS TO FEDERALLY SPONSORED RESEARCH, please insert the following paragraph: --This invention was made with government support under Contract No. AI 41768-14 awarded by the NIA. The government has certain rights in the invention.--

Signed and Sealed this

Twenty-eighth Day of August, 2007

JON W. DUDAS
*Director of the United States Patent and Trademark Office*